(12) United States Patent
Golding et al.

(10) Patent No.: US 7,700,273 B2
(45) Date of Patent: Apr. 20, 2010

(54) **PEPTIDOMIMETICS THAT MIMIC A CONFORMATIONAL-DEPENDENT NEUTRALIZING EPITOPE OF THE HUMAN IMMUNOD

| 1- Rabbit IgG only (12.5 µg/ml) | 2- Rabbit IgG + 25 µg/ml -2D7 | 3- Rabbit IgG + 125 µg/ml 2D7 |
| --- | --- | --- |
| 4- Rabbit IgG + 62.5 µg/ml 2D7 | 5- Rabbit IgG + 250 µg/ml 2D7 | |

(A) HUMAN PM1

(B) RHESUS PBMC (A)

(B)

(A)  (B)

PEPTIDOMIMETICS THAT MIMIC A CONFORMATIONAL-DEPENDENT NEUTRALIZING EPITOPE OF THE HUMAN IMMUNODEFICIENCY VIRUS (HIV) CCR5 CORECEPTOR

This application claims the benefit of the filing date of U.S. provisional application 60/560,703, filed Apr. 9, 2004, which is incorporated by reference herein in its entirety.

FIELD OF THE INVENTION

This invention relates, e.g., to peptides which closely mimic conformational epitopes recognized by monoclonal antibodies of interest, to nucleic acids encoding the peptides, and to monoclonal and polyclonal antibodies specific for the peptides.

BACKGROUND INFORMATION

Infectivity of certain viruses, particularly HIV and related viruses, such as SIV, SHIV and other immune deficiency viruses, is mediated by the co-receptor, CCR5. This co-receptor has been identified as a major target for HIV-1 entry inhibitors, since most of the viruses responsible for person to person transmission have been typed as CCR5-using (R5) strains. The naturally occurring Δ32 ccr5 allele, when homozygous, is associated with resistance to in vitro infection of $CD4^+$ cells with R5 viruses. Moreover, Δ32 ccr5 homozygosity confers considerable protection against HIV infection in vivo. Yet this genotype is not associated with abnormal immune function, and may be dispensable due to redundancy in chemokine receptor usage.

Three main classes of CCR5-targeting inhibitors have been reported: CC-chemokine analogues, small molecules, and monoclonal antibodies. One of the most active monoclonal antibodies targeting CCR5 is mAb 2D7, which was generated from the spleen of C57BL/6 nice immunized with the murine pre-B cell lymphoma line L1.2, which expresses high levels of transfected CCR5. This murine antibody was shown to inhibit in vitro infections of $CD4^+$ $CCR5^+$ human cells by most R5-tropic viruses at an $ID_{50}$ of 2-10 μg/ml, making it a good candidate for generating humanized antibodies. However, no success in humanizing this mAb has been reported. The epitope recognized by mAb 2D7 on CCR5 has been partially mapped to the first half of the second extracellular loop (ECL-2) by mutagenesis studies. Amino acids 171-KE-172 were found to be critical for mAb 2D7 binding. But the epitope was determined to be conformation-dependent, and the binding is lost in CCR5 mutants lacking the disulfide bridge between ECL-1 and ECL-2, as well as in reduced forms of CCR5 extracted from cells with various detergents.

It would be desirable to identify the conformational epitope recognized by mAb 2D7. A peptide that closely mimics this epitope could be useful, for example, for identifying a human monoclonal antibody against human CCR5. The peptide could also be useful for developing vaccines or other infection-blocking HIV-1 therapeutics.

DESCRIPTION OF THE DRAWINGS

FIG. 1 shows that selected phage clones react specifically with 2D7 in phage ELISA. Selection of phages expressing random 12-mer peptides was performed on mAb 2D7-coated plates. Clones p2D7-1 SK through p2D7-5SK were eluted from panning round IV and were analyzed for their binding to mAb 2D7 by phage ELISA as described in Example I.

FIG. 2 shows schematically the conformational structure of the 2D7 epitope on CCR5. The peptide sequences of four specific 2D7-binding phage clones (FIG. 1) from panning round IV were identical. Alignment of the phage-displayed peptide motif with CCR5 ECL-2 identified two regions of homology. These regions of homology are the underlined portions of the 2D7-2SK peptide sequence, E-W-Q-K-E-G-L-V-T-L-W-L (SEQ ID NO:1); the underlined Q-K-E-G-L segment is SEQ ID NO:2. The thread model of human CCR5 is adapted from Siciliano et al (1999) *J Biol Chem* 274, 1905-13.

FIG. 3 shows the characterization of mAb 2D7 binding to synthetic peptide 2D7-2SK peptide by ELISA. FIG. 3A shows direct binding of mAb 2D7 to different concentrations of biotinylated-2D7-2SK or to biotinylated-scrambled 2D7-2SK peptide (2D7-2SK-SCR) captured by streptavidin-coated microtiter plates. The bound antibodies were quantified by HRP-conjugated goat anti-mouse IgG antibody. FIG. 3B shows competition of binding of phages displaying peptide 2D7-2SK sequence (p2D7-2SK) to mAb 2D7 by soluble 2D7-2SK synthetic peptide. Microtiter wells, coated with mAb 2D7 at 200 ng/well, were incubated with serially diluted synthetic 2D7-2SK peptide or with a control peptide (CGRAARIGFPGAYTTKNG) (SEQ ID NO:3) for 30 min at room temperature. p2D7-2SK phages were then added to all wells ($10^9$ phages/well), followed by addition of HRP-conjugated anti-phage antibodies. FIG. 3C shows the identification of critical residues in the 2D7-2SK peptide sequence required for mAb 2D7 binding. MAb 2D7 (50 ng/100 μl/well) was added to plates coated with either unmodified biotin-2D7-2SK peptide or mutated biotin-2D7-2SK peptide derivatives (Table 1), all captured on streptavidin coated wells. The bound 2D7 antibodies were quantified by HRP-conjugated goat anti-mouse IgG antibody. The absorbance value (0.49) of mAb 2D7 binding to 2D7-2SK peptide (unmodified) is represented as 100% control binding.

FIG. 4 shows a Biacore sensogram for affinity measurements of mAb 2D7 binding to 2D7-2SK peptide. The sensogram shows mAb 2D7 binding to 2D7-2SK peptide immobilized on a CM5 sensor chip through the free thiol group. Several concentrations of 2D7 antibody were injected simultaneously onto both 2D7-2SK peptide and onto a third flow cell, which was free of peptide and used as a blank. As a control, anti-Ovalbumin antibodies were also injected at the same concentrations on the 2D7-2SK peptide-coupled chip, which showed no binding to this peptide.

FIG. 5 shows that preincubation with soluble 2D7-2SK peptide reduces the fusion inhibition activity of mAb 2D7. 2D7 antibody (at 10 μg/ml) was incubated for 1 h at 37° C. with 100-fold molar excess of different peptides before addition to CCR5 expressing PM1 cell for additional 1 h at 37° C. Effector 12E1 cells expressing BaL envelope were added, and syncytia were scored after 3 hrs. The number of syncytia (598/well) observed between E/T cells in absence of 2D7 antibody is represented as 100%. Fusion inhibition was compared with that of a control culture without IgG additives (PBS). Data shown are representative of four independent experiments. Standard deviations did not exceed 10% of the means for all groups. The 2D7-2SK peptide itself did not demonstrate any inhibitory activity in the fusion assay.

FIG. 6 shows the characterization of rabbit anti-2D7-2SK antibodies. IgG antibodies from rabbit immunized subcutaneously with KLH-conjugated 2D7-2SK peptide were used in peptide and Cell ELISA. FIG. 6A shows an experiment in which serial dilutions of rabbit anti-2D7-2SK antibodies (starting concentration of antibodies was 283 ng/ml) were added to biotinylated 2D7-2SK captured on streptavidin-coated wells and the binding was quantified by HRP-conjugated goat anti-rabbit IgG antibody. FIG. 6B shows the results when rabbit anti-2D7-2SK IgG (28.3 ng/ml) were added to the wells with cultured adherent control Cf2Th canine cells (CCR5$^-$) or Cf2Th cell line expressing CCR5 (CCR5$^+$). Specific antibody binding was measured by HRP-conjugated goat anti-rabbit IgG antibody.

FIG. 7 shows the detection of CCR5 expression by Rabbit anti-2D7-2SK antibodies using flow cytometry. Flow cytometry was used to detect Rab-anti-2D7-2SK binding to cell surface CCR5 protein expressed on CEM. NKR.CCR5 cells. Cells were incubated with 25 µg/ml concentrations of each antibody, which were detected with a FITC-labeled anti-mouse or rabbit IgG reporter antibody. Flow cytometry histograms from a representative experiment are shown: staining of CEM. NKR (thin lines) and CEM. NKR.CCR5 cells with anti-CCR5 mAbs (thick solid lines; mAb 2D7, or Rabbit anti-2D7-2SK) or isotype matched control mouse IgG, or with pre-immune rabbit IgG in the respective figures (dotted lines).

FIG. 8 shows steady-state equilibrium analysis of rabbit IgG binding to 2D7-2SK peptide by Biacore. Various concentrations of rabbit anti-2D7-2SK IgG antibody were injected simultaneously onto both 2D7-2SK peptide immobilized on a CM5 sensor chip through the free thiol group and onto a third flow cell, which was free of peptide and used as a blank. Binding was recorded using Biacore 3000 surface plasmon resonance biosensor instrument. As a control, Rabbit anti-anthrax PA antibodies were injected at the same concentrations on 2D7-2SK peptide coupled chip.

FIG. 9 shows dose-dependent reciprocal inhibition of mAb 2D7 and rabbit anti-2D7-2SK antibody binding to 2D7-2SK-coated biacore chips. FIG. 9A shows a surface plasmon resonance sensogram depicting binding of mAb 2D7 mixed with increasing concentrations of Rabbit anti-2D7-2SK IgG (Rab). Bound mAb 2D7 were detected by goat anti-mouse IgG. The baseline for the sensogram was normalized after injection of rabbit anti-2D7-2SK antibodies and 2D7 through the 2D7-2SK peptide coated chip. Therefore, the resonance units depicted are only due to the specific binding of anti-mouse IgG antibody to 2D7 so as to determine the association of mAb 2D7 to the 2D7-2SK peptide-coated chip in presence of increasing concentrations of rabbit anti-2D7-2SK antibodies. FIG. 9B shows a surface plasmon resonance sensogram depicting binding of rabbit anti-2D7-2SK peptide antibodies mixed with increasing concentrations of 2D7 mAb. Bound rabbit antibodies were detected with goat anti-rabbit IgG. The baseline for the sensogram was normalized as in FIG. 8A, but here the resonance units depicted are only due to the specific binding of anti-rabbit IgG antibody to rabbit anti-2D7-2SK antibodies so as to determine the association of rabbit anti-2D7-2SK antibodies to the 2D7-2SK peptide-coated chip in presence of increasing concentrations of 2D7.

FIG. 10 shows inhibition of HIV-1-env or SIV-env mediated cell fusion by rabbit anti-2D7-2SK antibodies. PM1 cells (FIG. 10A) or activated Rhesus PBMCs (FIG. 10B) were incubated for 1 h in the absence (PBS) or presence of 10 µg/ml of 2D7 antibody (2D7), rabbit anti-2D7-2SK IgG (affinity purified on peptide column) or control pre-bleed rabbit IgG, followed by addition of 12E1 cells expressing HIV-1 BaL envelope (FIG. 10A), or expressing SIV$_{mac239}$ envelope (FIG. 10B). Fusion inhibition was compared to the number of syncytia observed between E/T cells in absence of antibody (PBS) represented as 100%. Number of syncytia observed for fusion of 12E1 cells expressing HIV-1 BaL envelope and PM1 cells were 632/well, and for the fusion between Rhesus PBMCs and 12E1 cells expressing SIV$_{mac239}$ envelope were 270/well. Data shown is representative of one of three independent experiments. Standard deviations ranged between 5-10% of the means for all groups.

FIG. 11 shows the neutralization of HIV-1 infection by mAb 2D7 and rabbit anti-2D7-2SK peptide antibodies. (A) Antibody preparations (at 50 µg/ml) were added to CCR5 expressing PM1 cells or activated human PBMCs for 1 h prior to addition of R5 tropic HIV-1 BaL (or JR-CSF) virus at 100 TCID$_{50}$/well (5 replicates per group). After 24 hr plates were washed extensively to remove unbound virus and antibodies. Virus production was determined by measuring p24 in the supernatants every two days. Virus neutralization by the different antibodies is expressed as percent inhibition of p24 production (data represents average p24 values in 5 wells of 96-well plate). Data shown are for day 5 (PM1) or day 7 (PBMC). Infection inhibition was compared with that of a control cultures with no antibody added (PBS), which defined 100% infection (equivalent to p24 values of 64,484 pg/ml for HIV-1 BaL infection of PM1 cells and 40,567 pg/ml for infection of human PBMCs). Data shown are representative of one of four independent experiments for infection of PM1 cells and three independent experiments with human PBMCs. Dose dependent inhibition of infection by R5-tropic primary isolate 92US657 viruses of human PBMC's is shown in 'B'. The experiment was performed as in 'A' but with different concentrations of rabbit anti-2D7-2SK antibodies as shown on X-axis with infection by virus at 50 TCID$_5$/well (4 replicates per group). No inhibition was observed for control pre-immunized rabbit IgG.

FIG. 12 shows the binding of ScFv clones to the 2D7-2SK peptide. A cartoon of the binding molecules is shown in FIG. 12A. The binding data are shown in FIG. 12B.

FIG. 13 shows the binding of anti-2SK human ScFv's with 2D7-2SK in ELISA. A cartoon of the binding molecules is shown in FIG. 13A. The binding data are shown in FIG. 13B.

FIG. 14 shows the inhibition of HIV syncytia formation by anti-2SK human ScFv's.

FIG. 15 shows the specificity of fusion inhibition by anti-2SK human ScFv molecules. Significant fusion-inhibition of R5-env$^+$ cells (BaL and JR-FL) with CD4$^+$ CCR5$^+$PM1 cells was observed in the presence of anti-2SK human ScFv molecules. No inhibition of CXCR4-dependent fusion was observed. The 2D7-2SK selected ScFv human antibodies demonstrated the same specificity as the polyclonal rabbit antibodies and mouse mAb 2D7.

FIG. 16 shows that human anti-2SK-35 ScFv inhibits infection assays. The human ScFv inhibits HIV-1 (R5-tropic) replication to a similar degree as mouse monoclonal antibody 2D7. The data represent average p24 values in 5 wells of a 96-well plate.

DESCRIPTION OF THE INVENTION

Figure 1:
Figure 2:
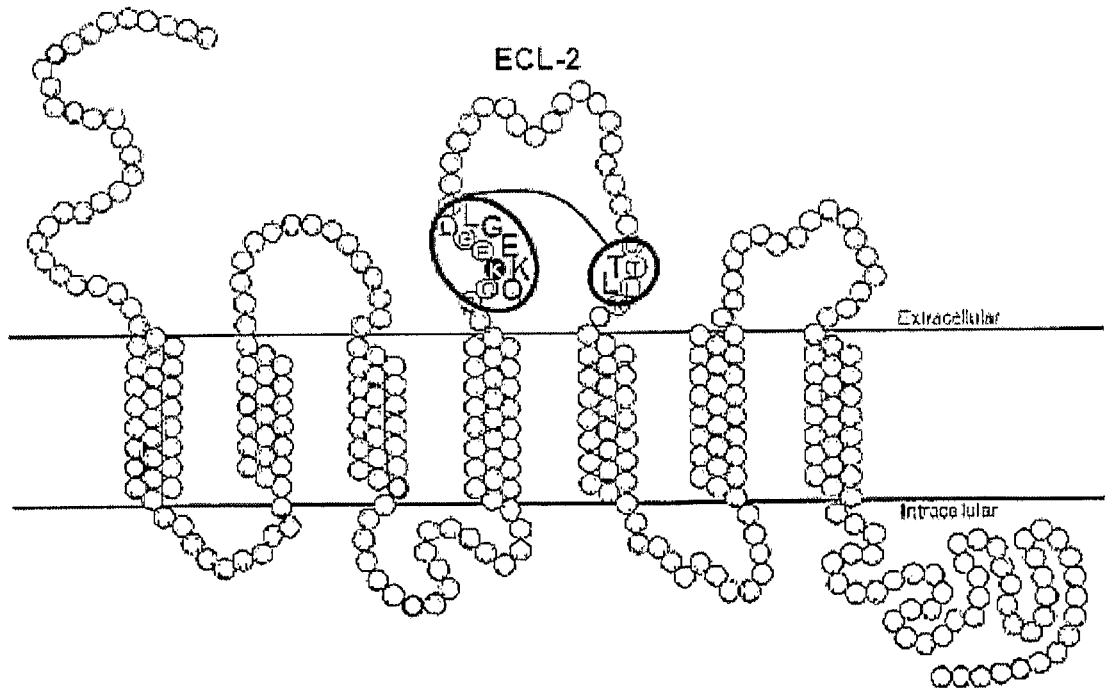

The inventors describe herein methods for identifying peptides which closely mimic conformational epitopes recognized by neutralizing monoclonal antibodies that bind to a pathogen or to a receptor or co-receptor on a cell targeted by the pathogen. In particular, methods are described for identifying peptides which closely mimic conformational epitopes recognized by a neutralizing monoclonal antibody (mAb) that binds to the HIV co-receptor CCR5 (e.g., the murine mAb 2D7). Briefly, the method comprises screening (panning) a random peptide library (such as a peptide phage display library) for peptides that bind preferentially and with high affinity (avidity) to a mAb of interest (e.g., 2D7). In one embodiment, the panning is performed in culture medium, such as EMEM (Eagle's Modified Eagles Medium) supplemented with serum (e.g., FBS). This differs from more conventional panning procedures, in which the panning is performed in a buffer, such as PBS. In another embodiment, the panning is performed in a buffer or in culture medium; then candidate peptides are further screened with one or more relevant biological assays, such as the ability of the peptide to inhibit antibody blocking of viral fusion (syncytia formation) or entry of the virus into a target cell. Following the panning and optional further screening, a candidate peptide is tested for its ability to produce a neutralizing antibody (such as a human antibody) against HIV (or SIV, SHIV, etc.), or against another pathogen of interest. One aspect of the invention is a neutralizing antibody produced by a method as above.

Example II shows that a peptide (represented by SEQ ID NO:1) identified by a method of the invention, which closely mimics a conformational epitope of CCR5, binds to mAb 2D7 with high affinity and can significantly reduce 2D7's ability to bind to CCR5 and block HIV-1 fusion. This peptide was conjugated to the adjuvant KLH and used to immunize rabbits, thereby generating polyclonal antibodies that bound to the HIV co-receptor and blocked HIV fusion and infection of target cells, including peripheral blood lymphocytes, from human and monkeys.

Another aspect of the invention is an isolated peptide comprising a sequence that is at least about 60% identical (e.g., at least about 60%, 65%, 70%, 75%, 80%, 85%, 90%, 95%, 98% or 100% identical) to the sequence E-W-Q-K-E-G-L-V-T-L-W-L (Glu-Trp-Gln-Lys-Glu-Gly-Leu-Val-Thr-Leu-Trp-Leu) (SEQ ID NO:1) over its entire length. That is, the contiguous amino acid residues of that sequence of the peptide are at least about 60% identical to the contiguous amino acids of SEQ ID NO:1. For example, the peptide may have about 1-3 internally located amino acid insertions, deletions or substitutions compared to SEQ ID NO:1 and/or the peptide may lack about 1-3 amino acids from one of both termini of SEQ ID NO:1. Another aspect of the invention is an isolated peptide which is an active variant of a peptide comprising SEQ ID NO:1. For example, the peptide may have about 1-3 internally located amino acid insertions, deletions or substitutions compared to SEQ ID NO:1 and/or the peptide may lack about 1-3 amino acids from one of both termini of SEQ ID NO:1. In one embodiment, a peptide comprising a sequence that is about 60% identical to SEQ ID NO: 1 is limited in size, e.g. it is no more than about 100, 80, 60, 50, 40, 30 or 20 amino acids in length. In another embodiment, the isolated peptide consists of SEQ ID NO:1, or consists of a sequence that is an active variant of SEQ ID NO:1 and/or is at least about 60% identical (e.g., at least about 60%, 65%, 70%, 75%, 80%, 85%, 90%, 95%, 98% or 100% identical) to the contiguous amino acid sequence of SEQ ID NO:1. Embodiments of the invention include peptides that differ by 1 amino acid from SEQ ID NO:1 (are about 92% identical to it) or that differ by 2 amino acids (are about 83% identical); by 3 amino acids (about 75% identical); by 4 amino acids (about 67% identical) or by 5 amino acids (about 60% identical). An active variant peptide of the invention (e.g. a peptide that exhibits the % identity to SEQ ID NO:1 discussed above) will maintain a biological function exhibited by a peptide comprising SEQ ID NO:1. For example, the variant peptide may bind preferentially and with high affinity to a mAb that binds to a conformational epitope of CCR5 that is involved in HIV, SHIV or SIV infection; and/or it may bind preferentially and with high affinity to mAb 2D7.

Other aspects of the invention include an isolated nucleic acid encoding a peptide of the invention; a vector comprising a nucleic acid of the invention, operably linked to an expression control sequence; a host cell comprising such a nucleic acid or vector; and a method for producing a peptide of the invention, comprising incubating such a host cell under conditions effective for expressing the peptide. Optionally, when the host cell is in with the method may further comprise harvesting the peptide in order to produce the peptide for further use. The host cell may be in vivo (in an animal). The introduction of the nucleic acid or vector into a cell in vivo, followed by production of the peptide in the animal, can be a method of DNA immunization.

Another aspect of the invention is an antibody (e.g., a neutralizing antibody) that binds preferentially and with high affinity to a peptide of the invention, provided that the antibody is not mAb 2D7, as disclosed in Wu et al. (1997) *J Exp Med* 186, 1373-81. Other antibodies that can be excluded from the invention include the following antibodies that have been reported to bind to CCR5, or derivatives of these antibodies: antibody A1 reported by Zhang et al: (2004) *Biochemistry* 43, 12575-12584, and antibody PRO-140 reported by Trkola et al. (2001) *J Virol* 75, 579-88. An antibody that does not exhibit the spectrum of cross-reactivities (e.g. to CCR5's from different organisms) or binding affinity to CCR5 exhibited by the antibodies of the invention is also excluded.

An antibody of the invention may be, e.g., polyclonal; monoclonal; a single chain monoclonal antibody; a whole (full size, bivalent) antibody, such as an IgG antibody; a suitable antibody fragment; a miniantibody; an antibody fusion product; humanized; camelized; and/or human. In embodiments of the invention, the antibody binds preferentially and with high affinity to a non-human primate protein, to a human protein, and/or to a receptor or co-receptor for HIV (e.g., HIV-1 or HIV-2), SIV, SHIV or another suitable immunodeficiency virus. Preferably, the antibody binds preferentially and with high affinity to human or monkey CCR5 and is a neutralizing antibody which blocks infection by HIV, SHIV, SIV or another suitable virus. Antibodies that block infection by strains or variants of these viruses (e.g., drug resistant variants or variants that have arisen as a result of genetic drift) are included. In a preferred embodiment, the antibody is a human, neutralizing, fall size monoclonal antibody specific for CCR5, and/or for a conformational epitope thereof, which blocks infection by HIV.

An antibody of the invention may be conjugated to an effector molecule, such as a toxin or a therapeutic agent that inhibits HIV, SHIV or SIV infection.

Another aspect of the invention is a pharmaceutical composition, comprising a peptide, nucleic acid or antibody of the invention and a pharmaceutically acceptable carrier.

Another aspect of the invention is a method for identifying and/or producing a polyclonal antibody (e.g. a neutralizing antibody) against a pathogen of interest (e.g., HIV), comprising introducing a peptide of the invention into an animal (such as a mouse, rat, rabbit, non-human primate or human), under conditions effective to produce an antibody specific for that peptide. Optionally, the method further comprises harvesting the antibody. Additional steps may be carried out to generate a monoclonal antibody and/or a human or humanized version of the polyclonal antibody.

Another aspect of the invention is a method for identifying an antibody (e.g., a monoclonal antibody), which is preferably neutralizing against a pathogen of interest, such as HIV, comprising screening a library of antibodies (e.g., monoclonal antibodies) or of fragments of suitable antibodies, such as a human antibody phage display library, for the ability to bind preferentially and with high affinity (avidity) to a peptide of the invention. In a preferred embodiment, the library is a library of human single strand mAbs. The ability to quickly and efficiently screen monoclonal antibody libraries for human antibodies that are specific for a peptide of the invention is an advantage of the invention; human antibodies are less likely than murine or only partially humanized antibodies to elicit undesirable antibody reactions following introduction into a human subject.

Another aspect of the invention is a method for identifying a therapeutic agent which inhibits CCR5-mediated HIV infectivity (e.g., a method to identify an antagonist or ligand of CCR5), comprising identifying an agent that binds preferentially and with a high affinity to a peptide of the invention. Among the types of therapeutic agents that can be identified by this method are antibodies, such as monoclonal antibodies, and small molecules.

Antibodies or other putative inhibitory agents identified by the above methods may be screened further to determine if they inhibit one or more CCR5-mediated activities, such as syncytia formation; viral entry into a target cell; or other functional assays discussed herein. Candidate agents may be further tested for the ability to inhibit HIV infection of human and/or monkey cells, or to inhibit infectivity in animal models of HIV-AIDS.

Another aspect of the invention is a method to identify an immunogen that exhibits improved immunogenicity and/or a peptide that exhibits altered specificity compared to a peptide comprising SEQ ID NO:1. The method comprises modifying the peptide (e.g., generating a mutant peptide, for example by altering one or more of its amino acids, conjugating the peptide to an immunogenic agent, or the like) and determining if the modified peptide is more highly immunogenic, or exhibits a different specificity, than the starting peptide. Another aspect of the invention is a method to identify a peptide which acts as a more efficient blocker or antagonist of HIV infection than a peptide comprising SEQ ID NO:1, comprising modifying the sequence of SEQ ID NO:1 as described above. Methods for rational design of peptides, which can be employed to design structural mimics of a peptide of the invention, based on the sequence or structure of the peptide, are conventional. See, e.g., US application 2003/0180284; Takasaki et al. (1997) *Nat Biotech* 15, 1266-70; Teichmann et al. (1999) *Curr Opin Struct Biol* 9, 390-399; Schwartz et al. (1999) *J Mol Biol* 287, 983-999; Reineke et al. (1999) *Nat Biotech* 17, 271-275. Guidance regarding the types of alterations that can be tolerated, and preferred locations of amino acids that can be altered, is provided below.

Another aspect of the invention is a method for preventing or inhibiting a viral infection of a host, comprising administering to the host an effective amount of a peptide, nucleic acid, or antibody of the invention. The administration of a peptide or nucleic acid will give rise to a neutralizing antibody (e.g., is a method of vaccination) when performed under conditions effective for the peptide to elicit such antibody production, or for the nucleic acid to be transcribed and translated to generate sufficient amounts of the peptide to elicit such antibody production. A "neutralizing" antibody, as used herein, includes an antibody that binds preferentially and with high affinity to the CCR5 receptor and inhibits the infectivity of a virus whose infectivity is mediated by CCR5 (e.g., inhibits binding of the virus to the cell, virus-mediated fusion with a target cell, and/or conformational changes in the viral envelope necessary for infectivity). The administration of a neutralizing antibody, itself, inhibits viral infection directly. In a preferred embodiment, the antibody blocks HIV transmission, e.g., mother to child transmission; and/or is used for passive immunoprophylaxis, as a mucosal microbicide, and/or in immunotherapy of HIV-infected individuals.

The inhibition by a neutralizing peptide, nucleic acid or antibody of the invention may be prophylactic or therapeutic. The inhibition may be of infectivity and/or of a cytopathic effect of a viral infection. In a preferred embodiment, the virus is a human immunodeficiency virus, such as HIV (e.g., HIV-1 or HIV-2), or is SIV or SHIV. In embodiments of the invention, a peptide, nucleic acid or antibody of the invention is administered parenterally. In other embodiments, an antibody of the invention is administered topically, e.g., to the vagina, penis, rectum or mouth of the host. In embodiments of the invention, the formulation is an emulsion, a suspension, a solution, a gel, a cream, a paste, a foam, a lubricant, a spray, a suppository, a pessary, or a tampon; the formulation is in or on a contraceptive device, such as a condom, a diaphragm, a cervical cap, a vaginal ring, a dental darn, a sponge, or the like; and/or the formulation further comprises another antiviral agent, or an antibiotic agent (e.g., an antifungal agent or an antibacterial agent). The invention also relates to formulations, such as parenteral or topical formulations, as above.

Another aspect of the invention is a method for preventing or inhibiting infection of a target cell by a virus, and/or fusion of viruses or cells expressing the viral envelope, comprising contacting the cell with an antibody of the invention, under conditions effective to achieve such inhibition. In embodiments of this method, the target cell contains CCR5 on its surface; is PMBC; is a non-human primate or a human cell (preferably a human cell); or the target cell is in vitro or is in vivo (in an animal).

Another aspect of the invention is as method for producing an antibody against a peptide of the invention in an animal [e.g., a mammal, including laboratory animals (such as mouse, rat, rabbit or guinea pig), cat, dog, non-human primate or human], e.g., a method to produce an antibody against a conformational epitope of CCR5, comprising introducing into the animal a peptide or nucleic acid of the invention, under conditions effective to produce the antibody. In a preferred embodiment, the antibody formed is neutralizing for HIV, SHIV or SIV, and the method is an immunization procedure. A vaccine, comprising a peptide, nucleic acid or antibody of the invention, is also included.

Another aspect of the invention is a complex comprising an antibody of the invention and a molecule of CCR5. Such a complex can form in vitro, and can be used, e.g., to further study the nature of the infection by HIV of a target cell; or it can form in vivo, e.g., following administration of an antibody of the invention to a subject infected with, or susceptible to infection with, the virus.

Another aspect of the invention is a kit suitable for carrying out a method of the invention, comprising one or more isolated peptides, nucleic acids or antibodies of the invention. For example, a kit suitable for therapeutic or prophylactic treatment of a virus infection (e.g., an HIV infection) in a subject may further comprise a pharmaceutically acceptable carrier and, optionally, a container or packaging material.

Peptides, nucleic acids and antibodies of the invention can be used for experimental purposes. For example, they can be used to increase the understanding of the mechanisms by which HIV, CCR5 and/or the HIV receptor, CD4, interact, and in general to understand mechanisms of HIV infectivity; and/or they can be used for studies of CCR5 structure-function relationships. Such experimental studies can be performed in vitro or in vivo. The peptides are also useful for generating reagents, such as small molecules or antibodies, that can be used therapeutically, e.g. in humans. Peptides specific for monkey CCR5 and antibodies specific for such peptides are particularly useful in monkey animal models, for proof-of-concept studies on putative anti-HIV therapies. Labeled antibodies are useful, for example, diagnostically or to study mechanisms of HIV infection.

Advantages of the antibodies of the invention (whether administered directly or produced indirectly in response to administration of a nucleic acid or peptide) include that they act early in the viral cycle, e.g., to inhibit entry of a virus into a target cell. Thus, without wishing to be bound by any particular mechanism, it is suggested that inhibitors of the invention can function potentially at a variety of steps during the infection process, including to inhibit initial infection of target cells; to inhibit infection of newly produced, uninfected immune cells generated in the body in response to the virus-induced killing of infected cells; and/or to block cell-to-cell fusion. Another advantage of the antibodies of the invention is that they are not hampered by hypervariability of the gp120-neutralizing determinants, which contributes to the extreme strain-dependence of viral sensitivity to gp120-directed antibodies, another type of antiviral agent which is currently under investigation. A further advantage of the peptides, nucleic acids and antibodies of the invention is that they can be readily and inexpensively produced on a large-scale basis.

Certain humans who, in spite of long-term exposure to HIV fail to develop symptoms of AIDS, have been shown to be resistant to HIV infection and to harbor homozygous CCR5 mutations. In spite of these mutations, the subjects do not exhibit a pathological phenotype (e.g., they have normal inflammatory and immuno reactions). Therefore, it is likely that treatment to inhibit CCR5 molecules would result in few if any side effects. This is another advantage of the inhibitors and methods of the invention.

Another advantage of inhibitors of the invention is that they are likely to inhibit infectivity of a wide range of mutant or variant HIV, at least because only rarely do virus mutants arise which lie in the regions of the virus that are involved in CCR5-mediated infectivity. Therefore, the inhibitors of the invention are likely to exhibit a broad range of specificities. Furthermore, there is no evidence of record of mutant CCR5 molecules that are expressed on the cell surface which would fail to react with an antibody of the invention.

The invention includes methods for identifying a peptide which closely mimics a conformational epitope on the surface of a pathogen or on a receptor or co-receptor involved in the infection of a cell by the pathogen. By a peptide which "closely mimics" a conformational epitope is meant a peptide which, although it may not be 100% identical in sequence to the conformational epitope, is nevertheless able to induce a neutralizing antibody that binds preferentially and with high affinity to the conformational epitope; and/or is a peptide which binds preferentially and with high affinity to such a neutralizing antibody. A receptor or co-receptor that is "involved in" infection of a cell by a pathogen is one that interacts with the pathogen, directly or indirectly, and mediates infection by the pathogen. For example, the CCR5 co-receptor is involved in infection by HIV and related viruses. Suitable pathogens include viruses (e.g., HIV, the SARS coronavirus, Ebola virus, viruses or epidemiologic agents of other emerging diseases, etc.), bacteria, parasites, etc. Preferably, an antibody, such as a mAb, which is known to neutralize the pathogen (either by virtue of its interaction with the pathogen, itself, or with a receptor or co-receptor for the pathogen), is used to screen a peptide library (e.g., a random peptide display library). Suitable antibodies have been described, for example for the SARS virus and the Ebola virus. The discussion herein relates generally to conformational epitopes of CCR5 involved in infectivity of certain HIV-related viruses, particularly HIV, SHIV and SIV. However, it is to be understood that the invention also relates to other viruses whose infection is mediated by CCR5, as well as to the isolation and use of peptides which mimic conformational epitopes for other suitable pathogens.

In one embodiment, the invention comprises screening (panning) a peptide library, particularly a random peptide library, such as a random peptide phage display library, for a peptide that binds preferentially and with high affinity to a neutralizing antibody of interest, e.g., an antibody, such as a mAb, that is specific for a portion of CCR5 which is involved in HIV infectivity. Such a panning procedure may identify undesirable peptides, e.g., in the latter case, peptides which do not closely mimic the conformational epitope of CCR5, and/or which cannot induce or be recognized by the neutralizing antibody specific for CCR5. To identify the subset of peptides which comprise the desired neutralizing epitopes, the inventors have developed two modifications of conventional panning procedures. A "neutralizing epitope," as used herein, refers to an epitope that can induce or be recognized by a neutralizing antibody. A "neutralizing peptide" is a peptide that comprises such an epitope. A "neutralizing nucleic acid" is a nucleic acid that expresses such a neutralizing peptide.

The first modification is to perform the panning in cell or tissue culture medium, such as DMEM, EMEM, RPMI etc. which is supplemented with serum, such as CS, FCS, FBS or the like. Screening in culture medium mimics the natural conditions for the antibody mediated neutralizing activity in cell culture. A skilled worker will recognize which culture medium (e.g. which salts or nutrients, which serum, etc.) is appropriate for a particular screening assay. This method differs from conventional panning procedures, at least because the panning is not carried out in a buffer, such as PBS.

The second modification is to perform one or more secondary assays. For example, the peptides can be screened for the ability to compete with a neutralizing antibody (e.g., the mAb 2D7) in one or more relevant assays. For example, one can measure the ability of the peptide to block an inhibitory activity of the antibody in a fusion assay (such as a syncytia assay, or fusion of an HIV or SIV viral envelope with a CD4 and CCR5 expressing target cell), or in an assay to measure viral entry into a cell.

The inventors found, unexpectedly, that this modified panning procedure, comprising panning in culture medium and performing a secondary biological screen, identified a high percentage of desirable peptides. For example, when panning was carried out in culture medium, using the mAb 2D7, all four of the neutralizing peptides obtained that were sequenced comprised SEQ ID NO:1.

After conducting the panning and secondary screening assay(s), the peptide(s) can be tested for their neutralizing ability. A variety of suitable testing methods will be evident to the skilled worker. For example, the peptide(s) can be tested for the ability to induce neutralizing antibodies, or to block viral infection. In one embodiment, the peptides are inoculated into a species other than that from which the mAb used in the panning procedure was derived. The inventors show herein that peptides selected with a mAb from mouse (2D7) can, when inoculated into a rabbit, elicit protective antibodies.

As used herein, the term "peptide phage display library" refers to a library of peptides (preferably random peptides) displayed on the surface of filamentous phage. The affinity and activity of ligands (e.g., antibodies, such as mAbs) to the displayed target are easy to evaluate by known phage display techniques; and methods using cells and viruses, and propagating the same, are conventional. In some embodiments of the invention, antibody phage display libraries are used in which antibodies (such as single strand antibodies) or antibody fragments are displayed on the surface of filamentous phage.

A "conformational epitope" or "discontinuous epitope" is composed of different parts of a protein and is dependent on its secondary (e.g., alpha (α)-helices, beta (β)-sheets, turns, etc.) and/or tertiary structures (e.g., domains composed of alpha (α)-helices, beta (β)-sheets, turns, etc). In general, an antibody response against a conformational epitope is directed against the active (folded) form of the antigen. Such antibodies are preferable to antibodies directed against an unnatural, denatured form of the antigen. An antibody specific for a peptide that closely mimics a conformational epitope will generally also be specific for the intact protein containing the conformational epitope.

The term "isolated," as used herein, when referring, e.g., to a peptide, polynucleotide or antibody, means that the material is removed from its original environment (e.g., the natural environment if it is naturally occurring), and is isolated or separated from at least one other component with which it is naturally associated. For example, a naturally-occurring antibody present in its natural living host is not isolated, but the same antibody, separated from some or all of the coexisting materials in the natural system, is isolated. Such antibodies could be part of a composition, and still be isolated in that such composition is not part of its natural environment.

By a peptide binding "preferentially" or "specifically" to an antibody is meant that the peptide binds selectively to that antibody in comparison to other antibodies. Similarly, by an antibody binding "preferentially" or "specifically" to a peptide or protein is meant that the antibody binds selectively to that peptide or protein in comparison to other peptides or proteins. For example, an antibody of the invention may bind at least about 25% to 100 fold, or more, as efficiently to a peptide comprising SEQ ID NO:1 than it binds to a peptide comprising a scrambled sequence in place of SEQ ID NO:1, or to another baseline control. A peptide that binds with "high affinity" ("high avidity") to an antibody binds to it with a binding coefficient of less than about 100 nM, preferably in the lower nM range or pM range.

An antibody of the invention will bind preferentially and with high affinity to the peptide used to screen for the antibody by a method of the invention, or to a peptide against which the antibody was generated. However, the antibody may also bind to related, but not identical, conformational epitopes of CCR5 that are involved in binding to HIV, SHIV or SIV, and/or to peptides which closely mimic such conformational epitopes. For example, the Examples herein demonstrate cross-reactivity of antibodies generated against a "human-like" CCR5 with CCR5's from monkey, and vice-versa. In the discussion herein, an antibody is sometimes said to bind "preferentially" or "specifically" to a particular peptide. It is to be understood that the antibody may also bind with high affinity to a related conformational epitope, as discussed above.

As used herein, the singular forms "a," "an," and "the" include plural referents unless the context clearly dictates otherwise.

One aspect of the invention is an isolated peptide comprising a sequence that is at least about 60% identical to SEQ ID NO:1, wherein the peptide closely mimics a conformational epitope of CCR5 that is involved in HIV, SHIV or SIV infection. Some proteins which comprise sequences that are related to SEQ ID NO:1 are not encompassed by the invention. Among the proteins which are excluded are: the human and bovine sperm-specific PKA anchoring proteins (sequences 15 and 13) described in U.S. Pat. No. 6,451,528; the *Klebsiella pneumoniae*-related protein, sequence 10059 from U.S. Pat. No. 6,610,836; the unnamed human protein product listed in Genbank as gi/45503530/emb/CAF86779.1; the murine FcγR receptor protein, sequence 92 from U.S. Pat. No. 5,985,599; the unknown environmental sequence listed in Genbank as gi/42970691/gb/EAB52325; the plant protein listed in Genbank as gi/38347577/emb/CAE04978.2; the mouse protein similar to Tcra-J protein listed in Genbank as gi/38088553/ref/XP__356237.1; the unknown environmental sequence listed in Genbank as gi/43752522/gb/EAF30684.1; the unnamed mouse protein product listed in Genbank as gi/29244424/ref/NP__808509.1; the *B. Cereus* protein listed in Genbank as gi/29894035/gb/AAP07327.1; the coxsackie-adenovirus-receptor homolog listed in Genbank as gi/26345850/dbj/BAC36576.1; the *B. anthracis* protein listed in Genbank as gi/30253743/gb/AAP24285.1; the *B. Cereus* protein listed in Genbank as gi/42779347/ref/NP__976594.1; the ligase domain listed in Genbank as gi/21398191/ref/NP__654176.1; and the regulatory protein listed in Genbank as gi/14027993/dbj/BAB54585.1.

Another aspect of the invention is an isolated peptide that consists essentially of the contiguous amino acids of SEQ ID NO:1, or consists essentially of a sequence that is at least about 60% identical to the contiguous amino acids of SEQ ID NO:1. The term "consisting essentially of," when used in the present context, refers to a sequence which is intermediate in size between the number of amino acid residues encompassed by the term "consisting of" and the longer length encompassed by the term "comprising," and which does not affect the basic and novel characteristics of the peptide encompassed by the "consisting of" language. For example, in the present case the additional amino acids do not interfere with the property of the peptide to closely mimic a conformational epitope of the invention. A peptide that consists essentially of the contiguous amino acids of SEQ ID NO:1 generally has no more than about 100 amino acids, e.g. no more than about 60, 50, 40, 30 or 20 amino acids.

A variety of active variants of a peptide comprising SEQ ID NO:1 (e.g. active peptides comprising a sequence that is at least about 60% identical to the contiguous amino acids of SEQ ID NO:1) are encompassed by the invention. Such an "active" variant is one that exhibits a biological activity of a peptide comprising SEQ ID NO:1. For example, the peptide may bind to a CCR5-specific neutralizing monoclonal antibody of interest (e.g., 2D7) with approximately the same (or greater) specificity and affinity as does a peptide comprising the sequence of SEQ ID NO:1; and/or it may block a biologically relevant inhibitory activity of the mAb at least as well as a peptide comprising SEQ ID NO:1; and/or it may elicit (induce) a neutralizing antibody (e.g., an antibody which inhibits HIV infection) or block an activity of CCR5 that is related to viral infection, at least as efficiently as does the mAb. For example, such a peptide can inhibit 2D7-mediated blocking of infectivity or cytopathogenesis of an HIV virus, or can induce such an a neutralizing antibody having such properties. "Approximately the same" specificity or affinity, as used herein, means at least about 90% as much specificity or activity as the non-variant peptide.

Amino acids QKEGL (SEQ ID NO:2) (in positions 3-7 of SEQ ID NO:1) and TL (in positions 9-10) correspond to residues of CCR5 which are thought to be particularly important for infectivity of HIV or related viruses. Therefore, a variant peptide of the invention preferably contains at least about 3-4 of the contiguous amino acids QKEGL (SEQ ID NO:2), preferably at least the contiguous amino acids QKE, or homologous substitutions of one or more of those amino acids. Preferably, all five of the amino acids in this moiety are present. Furthermore, a variant peptide of the invention preferably contains a second moiety—at least one of the contiguous amino acids TL. More preferably, both of those amino acids are present. The spacing between these two moieties in SEQ ID NO:1 can also be modified. For example, about 1-3 amino acid insertions or deletions can be introduced between them, provided the peptide retains the ability to closely mimic a conformational epitope of the invention, e.g. provided that the peptide maintains the overall structure or conformation of the peptide. In one embodiment, the contiguous amino acids in the QKEGL (SEQ ID NO:2) sequence and the contiguous amino acids TL are both present in the peptide. One of skill in the art can readily design peptides and determine if they retain the desired activity, using conventional, routine procedures. In general, the discussion herein refers to a "peptide of the invention." It is to be understood that active variants of the peptide, including a peptide comprising a sequence that is at least about 60% identical to the contiguous sequence SEQ ID NO:1, are also included.

The invention encompasses active length variants which lack one or more amino acids from one or both ends of SEQ ID NO:1. Active variants comprising about 6-11 contiguous amino acids of SEQ ID NO:1 are included in the invention. As used herein, the terms "peptide," "polypeptide," and "protein" are used interchangeably; the term does not imply any restriction as to length. Fusion proteins of the invention may also be of any length that is compatible with the invention.

The invention also encompasses active sequence variants, which comprise variants of the contiguous sequence of SEQ ID NO:1. Sequence variants of the invention include any of a variety of alterations (changes, modifications, mutations), provided that the changes do not substantially alter desirable functional properties of the peptide. The changes can be within the 5-mer sequence, QKEGL (SEQ ID NO:2) or the dimer, TL; or they can be in other portions of SEQ ID NO:1. Preferably, the alterations are not in the QKEGL (SEQ ID NO:2) or TL sequences. In one embodiment of the invention, the peptide comprises no more than one or two homologous substitutions in the contiguous amino acids of the QKEGL (SEQ ID NO:2) moiety and/or no more than one homologous substitution in the contiguous TL moiety. One of skill in the art can readily determine if a given variant retains suitable activity, using conventional methods.

Sequence variants of the invention include peptides having one or more naturally occurring (e.g., through natural mutation) or non-naturally-occurring (e.g., by deliberate modification, such as by site-directed mutagenesis) modifications, e.g., insertions, deletions, additions and/or substitutions, either conservative or non-conservative. By "conservative substitutions" is meant by combinations such as Gly, Ala; Val, Ile, Leu; Asp, Glu; Asn, Gln; Ser, Thr; Lys, Arg; and Phe, Tyr. Preferably, the modification is a conservative amino acid substitution. Variants can include, e.g., homologs, muteins and mimetics. The invention also encompasses variants reflecting genetic polymorphism (e.g., allelic variation).

Methods to determine sequence identity (between nucleic acids or proteins) are conventional. Alignments can be accomplished by using any effective algorithm. For pairwise alignments of DNA sequences, the methods described by Wilbur-Lipman (e.g., Wilbur et al. (1983), *Proc. Natl. Acad. Sci.*, 80, 726-730) or Martinez/Needleman-Wunsch (e.g., Martinez (1983), *Nucleic Acid Res.* 11, 4629-4634) can be used. Pairs of protein sequences can be aligned by the Lipman-Pearson method (e.g., Lipman et al. (1985), *Science* 227, 1435-1441), e.g., with k-tuple set at 2, gap penalty set at 4, and gap length penalty set at 12. Various commercial and free sources of alignment programs are available, e.g., MegAlign by DNA Star, BLAST (National Center for Biotechnology Information), BCM (Baylor College of Medicine) Launcher, etc. Percent sequence identity can also be determined by other conventional methods, e.g., as described in Altschul et al. (1986), *Bull. Math. Bio.* 48, 603-616, 1986 and Henikoff et al. (1992), *Proc. Natl. Acad. Sci. USA* 89, 10915-10919.

Other types of active variant peptides of the invention include one or more of various types of protein modifications, including post-translational modifications. Post-translational modifications include naturally occurring or synthetically produced, covalent or aggregative conjugates with other chemical moieties, e.g., glycosyl groups, lipids, peptides, phosphates, acetyl groups, etc., as well as cleavage, such as of terminal amino acid(s). See, e.g., modifications disclosed in U.S. Pat. No. 5,935,835. A variety of chemical modifications may be introduced which enhance the stability of a peptide of the invention. See, e.g., Wunsch (1983) *Biopolymers* 22, 493-505 and Samanen, in Polymeric Materials in Medication, Gebelein et al, eds, Plenum Press: New York, 1985, pp. 227-242. Among possible options for useful chemical modifications include, e.g., olefin substitution, carbonyl reduction, D-amino acid substitution, N-methyl substitution, C-methyl substitution, C—C'-methylene insertion, dehydro amino acid insertion, retro-inverso modification, N-terminal to C-terminal cyclization, and thiomethylene modification. Peptides of the invention can also be modified by covalent attachment of carbohydrates and polyoxyethylene derivatives, which are expected to enhance stability and resistance to proteolysis. See, e.g., Abuchowski et al., in Enzymes as Drugs, Holcenberg et al., eds, John Wiley: New York, 1981, pp. 367-378. Other active variants may comprise added peptide sequences, either naturally occurring or heterologous, such as, e.g., leader, signal, secretory, targeting, enzymatic etc. sequences.

Other active variant peptides comprise agents that enhance immunogenicity of the peptide (e.g., attachment to KLH, MAP (multiple antigenic peptide), alum, other antigens, lipids, toxoids, CpGs, etc. or other well-known, conventional agents or adjuvants); improve stability of the peptide; increase the half-life of the peptide; increase resistance of the peptide to proteolysis; decrease the rate of in vivo clearance of the peptide; provide a means to attach or immobilize a peptide of the invention onto a solid support matrix (see, e.g., Harris, in Poly(Ethylene Glycol) Chemistry: Biotechnical and Biomedical Applications, Harris, ed., Plenum Press: New York (1992), pp. 1-14); or the like. Suitable such agents include, e.g., polyethylene glycol, dextran, albumin, etc.

Other active variant peptides may take the form of cyclic peptides, branched peptides, peptomers (cross-linked peptide polymers) or other complex multimeric structures.

Peptides of the invention can be prepared by a variety of conventional procedures, which will be evident to a skilled worker. For example, one can clone a suitable polynucleotide and express the peptide recombinantly; one can generate the peptide synthetically; or one can cleave a longer peptide, using suitable proteases or biochemical cleavage procedures. Combinations of these methods can also be used.

In a preferred embodiment, the peptide is synthesized chemically, using a conventional, routine procedure. Typical procedures are described, e.g., in Principles of Peptide Synthesis (Springer Laboratory), ed. Bodanszky, Springer Verlag, $2^{nd}$ edition, 1993.

Alternatively, one can clone a nucleic acid encoding the peptide into a vector, introduce the vector into a suitable prokaryotic or eukaryotic host cell, culture the cell under conditions effective for expression of the peptide, and harvest the peptide from the cell. Suitable host cells include, e.g., bacteria, yeast, insects, mammalian or plant cells. The recombinant polypeptide can also be expressed in a transgenic plant or non-human animal. Methods for cloning and expressing peptides and polypeptides are routine and conventional. For general references describing methods of molecular biology which are mentioned in this application, e.g., isolating, cloning, modifying, labeling, manipulating, sequencing and otherwise treating or analyzing nucleic acids and/or proteins, see, e.g., Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elseveir Sciences Publishing, Inc., New York; Hames et al. (1985), *Nucleic Acid Hybridization*, IL Press; Dracopoli et al. *Current Protocols in Human Genetics*, John Wiley & Sons, Inc.; and Coligan et al. *Current Protocols in Protein Science*, John Wiley & Sons, Inc. The methods described herein with regard to cloning and expressing a peptide of the invention, e.g. a peptide that closely mimics a conformational epitope of interest, can also be used for cloning and expressing an antibody of the invention or an antibody fragment of the invention.

In a preferred embodiment, a sequence coding for a peptide of the invention is placed under the control of an expression control sequence. The phrase "expression control sequence" means a polynucleotide sequence that regulates expression of a peptide or polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Novagen have been designed to permit a molecule to be inserted into all three reading frames to identify the one that results in polypeptide expression). Expression control sequences can be heterologous or endogenous to the normal gene. Vectors in which a sequence of interest is placed under the control of an expression control sequence are sometimes referred to as "expression vectors."

As used herein, the term "conditions effective for expression" of a peptide means, in part, that the nucleic acid encoding it comprises expression control sequences that allow transcription of a DNA into RNA and translation of an RNA into a peptide. Effective conditions for expression of a peptide include any conditions which are suitable for achieving production of the peptide, including effective temperatures, pH, salts, or the like.

The cloned nucleic acids, in a suitable vector, can be "introduced" into a cell by any of a variety of conventional, art-recognized procedures, including, e.g., transfection (e.g., mediated by DEAE-Dextran or calcium phosphate precipitation), infection via a viral vector (e.g., retrovirus, adenovirus, adeno-associated virus, lentivirus, pseudotyped retrovirus or poxvirus vectors), injection, electroporation, transformation, sonoporation, a gene gun, liposome delivery (e.g., Lipofectin®, Lipofectamine® (GIBCO-BRL, Inc., Gaithersburg, Md.), Superfect® (Qiagen, Inc. Hilden, Germany) and Transfectam® (Promega Biotec, Inc., Madison, Wis.), or other liposomes developed according to procedures standard in the art), or receptor-mediated and other endocytosis mechanisms.

The preceding methods for producing a peptide of the invention can be employed for generating large quantities of the peptide; or they can be employed as a method for producing the peptide in a host (e.g., a DNA vaccine).

Another aspect of the invention is a polynucleotide encoding a peptide of the invention. Some suitable polynucleotides are discussed above, with regard to recombinant technology. As used herein, the terms "nucleic acid" and "polynucleotide" are interchangeable. A nucleic acid or polynucleotide can be of any length that is compatible with the invention.

Nucleic acids encoding peptides of the invention may comprise additional polynucleotide sequences, e.g., sequences to enhance expression, detection, uptake, cataloging, tagging, etc. For example, the polynucleotide may contain additional non-naturally occurring or heterologous coding sequences (e.g., sequences coding for leader, signal, secretory, targeting, enzymatic, fluorescent, antibiotic resistance, and other functional or diagnostic peptides) or non-coding sequences (e.g., untranslated sequences at either a 5' or 3' end).

Another aspect of the invention is an antibody (e.g., a neutralizing antibody) generated against, and/or specific for, a peptide of the invention. Antibodies of the invention provide the basis for a wide variety of prophylactic or therapeutic uses, qualitative and quantitative analytical methods, separation and purification methods, and other useful applications directed to the subject peptides. The antibodies can be used in vitro or in vivo. It will be readily apparent to one skilled in the art that antibodies generated against, or specific for, a peptide of the present invention can be prepared using well-established methodologies (e.g., the methodologies described by Harlow et al. in Antibodies. A Laboratory Manual, Cold Spring Harbor Laboratory, Cold Spring Harbor, 1988, pp. 1-725). Such antibodies can comprise polyclonal or monoclonal antibodies, or fragments thereof. Furthermore, such antibodies can be obtained and employed either in solution-phase or coupled to a desired solid-phase matrix, such as a condom.

Example II describes the isolation and characterization of polyclonal rabbit antibodies generated against a peptide consisting of SEQ ID NO:1. This peptide is sometimes referred to herein as 2D7-2SK. The rabbit polyclonal antibodies are useful, for example, as an anti CCR5 tool for experimental purposes.

Example III describes the isolation and characterization of single chain human monoclonal antibodies against the peptide 2D7-2SK, in particular, the two most efficient antibodies, ScFv-2SK-34 and ScFv-2SK-35. These latter two antibodies are sometimes referred to herein as ScFv-SK34 and ScFv-SK35, respectively. The single chain mAbs were isolated using a synthetic human single chain human IgG library provided by Itai Benhar, University of Tel Aviv. The human mAbs are useful, for example, as in vitro reagents for experimental or diagnostic purposes, or for in viva prophylaxis or therapy. The invention relates not only to these single chain mAbs, but also to nucleic acids encoding and expressing them, and cell lines expressing those DNAs to produce the antibodies. Example III also describes the isolation and characterization of complete (bivalent) human monoclonal antibodies generated from the ScFv's, ScFv-SK-34 and ScFv- SK-35. In general, the complete mAbs are preferable to the respective ScFv's, especially for in vivo uses.

Example IV describes a peptide which mimics a conformational epitope of Rhesus Macaque (sometimes referred to herein as Rhesus) CCR5, and the isolation and characterization of rabbit polyclonal antibodies generated against this peptide.

An antibody of the invention can be introduced directly into (or onto a mucosal surface of) a subject. Alternatively, a peptide or nucleic acid of the invention can be introduced into a subject, in order to generate an antibody (e.g. a method of vaccination). The subject (e.g., patient) can be any animal which suffers from, or is at risk for developing, an infection by a pathogen of interest. For example, a suitable subject is an animal infected with (therapeutic), or at risk for being infected with (prophylactic), HIV or another virus whose infectivity is mediated by CCR5. A suitable subject may be one in which the generation of an antibody (e.g., as a result of the introduction of a peptide of the invention, or a nucleic acid expressing the peptide) would ameliorate an infection, such as a CCR5-mediated infection by HIV. Suitable subjects include, e.g., a cat, dog, horse, bird, rodent, non-human primate or human. The method can treat, inhibit, or prevent an infection or cytopathology and/or can ameliorate symptoms associated with such infections.

In one embodiment, an antibody of the invention is used as a targeting molecule to deliver an effector molecule, such as a toxin or therapeutic substance (e.g., drug), to a cell which expresses a receptor or co-receptor for a pathogen (e.g., CCR5) on its surface. The toxin or therapeutic substance is attached to (e.g., conjugated to, bound to) the antibody in such a way that it does not substantially disturb the ability of the antigen-binding region to bind to its targets. For example, the effector can be attached to an Fc region. Alternatively, when the effector is in the form of a peptide, it can replace all or part of an Fc region, or it can substitute for part or all of an antigen-binding region of a third antibody moiety, forming a structure similar to a third Fab fragment. An antibody (or other targeting molecule) attached to an effector molecule is sometimes referred to as a "chimeric" molecule.

Antibodies conjugated to toxic or therapeutic moieties need not be neutralizing. Rather, they can serve to deliver a molecule to a target cell, so that the molecule can exert its effect at the surface of the cell, or be incorporated into the cell.

An effector molecule can be any substance which inhibits infection and/or replication by a pathogen of interest. The present discussion relates to the inhibition of HIV in a cell bearing an CCR5 receptor or receptor subunit on its surface, but it is to be understood that this discussion relates to the inhibition of any pathogen. An effector molecule can be any substance which inhibits infection by HIV of a cell bearing a CCR5 receptor or receptor subunit on its surface, and/or which achieves inhibition, destruction, killing etc. of such a cell, which is infected by HIV. Any effective effector molecule can be used, including an agent that is used currently to treat HIV-AIDS, but is delivered to the cell by another method. The effector molecule can be isolated from natural sources, or it can be produced by synthetic and/or recombinant means, all of which are well-known to one of ordinary skill in the art. Among the drugs or therapeutic moieties which can be used to inhibit viral replication are reverse transcriptase inhibitors, protease inhibitors, etc. Some suitable types of agents are discussed elsewhere herein.

Toxins can be attached to an antibody in order to inhibit, destroy or kill infected cells. Among the many toxins which can be used are, e.g., ricin (e.g., the A and/or B chain thereof, or the deglycosylated form), poisonous lectins, diphtheria toxin, exotoxin from *Pseudomonas aeruginosa*, abrin, modeccin, botulina toxin, alpha-amanitan, pokeweed antiviral protein (PAP, including PAPI, PAPII and PAP-S), ribosome inhibiting proteins, especially the ribosome inhibiting proteins of barley, wheat, corn, rye, or gelonin, ribosome-inactivating glycoprotein (GPIR), doxorubicin, maytansinoids, vinblastine, cisplatin, pirarubicin, melphalan, daunomycin, genistein, cytotoxic prodrugs, antisense molecule, ribonucleases (e.g., Ribonuclease A), or the like. Fragments, subunits, muteins, mimetics, variants and/or analogues of such toxins are known to those of skill in the art and are encompassed by the invention. It is contemplated that all such variants or mutants which retain their toxic properties will be of use in accordance with the present invention. For a further discussion of suitable cytotoxins, see U.S. Pat. No. 6,428,788.

Other therapeutic moieties include liposomes or micelles that contain a therapeutic composition such as a drug, a nucleic acid, or another therapeutic moiety that is preferably shielded from direct exposure to the circulatory system. Means of preparing liposomes attached to antibodies are well known to those of skill in the art. See, for example, U.S. Pat. No. 4,957,735 or Connor et al. (1985) *Pharm. Ther.* 28, 341-365.

In another embodiment, the effector molecule comprises any of a variety of art-recognized radioisotopes or radionuclides. Methods of radiotherapy (nuclear medicine), in which cytotoxic doses of radioactivity are delivered to cells, are conventional in the art and are described, e.g., in EP 481,526; U.S. Pat. No. 5,962,424; Roeske et al (1990) *Int. J Radiation Oncology Biol. Phys.* 19, 1539-48; and Leichner et al(1993) *Med. Phys.* 20(2Pt.2), 569-77. Among the most preferred radiation sources are Tc-99 and In-111.

Other effector molecules do not exhibit a therapeutic property, per se, but act to stabilize the antibody or another attached effector molecule, e.g. improve its stability; increase its half-life; increase its resistance to proteolysis; increase or decrease its immunogenicity; decrease the rate of its in vivo clearance; provide a means to attach or immobilize an antibody or antibody/effector conjugate of the invention onto a solid support matrix; or the like. Suitable such agents include, e.g., polyethylene glycol, dextran, albumin, etc.

Antibodies of the invention can be coupled to more than one effector molecule, each of which, optionally, can have different effector functions (e.g., such as a toxin molecule and a stabilizing agent). In another embodiment, antibodies comprising two or more different effector molecules are administered together.

An effector molecule can be attached to an antibody of the invention by routine, conventional methods, e.g., chemical coupling, attachment via biotin/avidin interactions or a peptide linker, recombinant methods, etc. For a discussion of some suitable attachment methods, see, e.g., US publication 2002/0025317, U.S. Pat. No. 6,428,788, or WO00/54805.

One embodiment of the invention is a method for preventing or inhibiting viral infection in a subject in need thereof, comprising administering an antiviral effective amount of an above-described peptide, nucleic acid or antibody (any of which is sometimes referred to herein as an "inhibitory agent" of the invention), under conditions effective to achieve inhibition of the viral infection. Suitable effective conditions will be evident to a skilled worker. For example, for immunization with a peptide of the invention, a suitable adjuvant will generally be present, either attached to the peptide or co-administered with it, to enhance the production of a neutralizing antibody.

In another embodiment, the method comprises inhibiting (e.g., preventing) sexual transmission of viral infection, e.g., HIV infection, comprising vaginal, rectal, oral, penile, or other topical, insertional, or instillational treatment with an antiviral effective amount of an antibody of the invention, alone or in combination with another antiviral compound.

In another embodiment, an antibody of the invention is used to inhibit mother-to-child transmission of HIV. To inhibit such transmission during birth, the antibody can be administered during birth or to the newborn infant. Alternatively, the antibody can be administered to block transmission through mother's milk. Any of these methods can, of course, be used in conjunction with the administration of other antiviral agents.

A number of considerations are generally taken into account in designing delivery systems, routes of administration, and formulations for protein and peptide drugs, such as the peptides of the invention which are used as inocula to generate antibodies. See, e.g., Eppstein (1988), *CRC Crit. Rev. Therapeutic Drug Carrier Systems* 5, 99-139; Siddiqui et al. (1987), *CRC Crit. Rev. Therapeutic Drug Carrier Systems* 3, 195-208, 1987); Banga et al. (1988), *Init. J. Pharmaceutics* 48, 15-50; Sanders (1990), *Eur. J. Drug Metab. Pharmacokinetics* 15, 95-102; and Verhoef (1990), *Eur. J. Drug Metab. Pharmaco-kinetics* 15, 83-93. The appropriate delivery system for a given peptide of the invention will depend, e.g., upon its particular nature, formulation, etc. As with any protein or peptide drug, oral delivery of a peptide of the invention will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it is preferable to use an absorption-enhancing agent in combination with a given peptide of the invention. A wide variety of absorption-enhancing agents have been investigated and/or applied in combination with protein and peptide drugs for oral delivery and for delivery by other routes (Verhoef, 1990, supra; van Hoogdalem (1989), *Pharmac. Ther.* 44, 407-443; Davis, J. (1992) *Pharm. Pharmacol.* 44(Suppl. 1), 186-190). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycolate and taurocholate, and derivatives, such as taurodihydrofusidate, (d) fatty acids, such as oleic acid and capric acid, and their derivatives, such as acylcarnitines, monoglycerides and diglycerides, (e) non-surfactants, such as unsaturated cyclic ureas, (f) saponins, (g) cyclodextrins, and (h) phospholipids.

Other approaches to enhancing oral delivery of peptides can include aforementioned chemical modifications to enhance stability to gastrointestinal enzymes and/or increased lipophilicity. Alternatively, or in addition, the peptide can be administered in combination with other drugs or substances, which directly inhibit proteases and/or other potential sources of enzymatic degradation of proteins and peptides. Yet another alternative approach to prevent or delay gastrointestinal absorption of protein or peptide drugs, such as peptides of the invention, is to incorporate them into a delivery system that is designed to protect the protein or peptide from contact with the proteolytic enzymes in the intestinal lumen and to release the intact protein or peptide only upon reaching an area favorable for its absorption. A more specific example of this strategy is the use of biodegradable microcapsules or microspheres, both to protect vulnerable drugs from degradation, as well as to effect a prolonged release of active drug (Deasy, in Microencapsulation and Related Processes, Swarbrick, ed., Marcell Dekker, Inc.: New York, 1984, pp. 1-60, 88-89, 208-211). Microcapsules also can provide a useful way to effect a prolonged delivery of a peptide of the invention, after injection (Maulding, J. (1987) *Controlled Release* 6, 167-176).

There are numerous other potential routes of delivery, which are suitable for delivering (e.g., introducing into a subject) nucleic acids or peptides of the invention which serve to generate an immune response in a host (e.g., when used as vaccines); or for delivering an antibody to a host. These routes include intravenous, intraarterial, intrathecal, intracisternal, intramuscular, intraperitoneal, buccal, rectal, nasal, pulmonary, transdermal, vaginal, ocular, transdermal, extracorporeal, and the like (See, e.g., Eppstein, 1988, supra; Siddiqui et al., 1987, supra; Banga et al., 1988, supra; Sanders, 1990, supra; Verhoef, 1990, supra; Barry, in Delivery Systems for Peptide Drugs, Davis et al., eds., Plenum Press: New York, 1986, pp. 265-275; and Patton et al. (1992), *Adv. Drug Delivery Rev.* 8, 179-196). In a preferred embodiment for the administration of an antibody of the invention, topical administration is used e.g., vaginal, rectal, penile, to the mouth, or other topical treatment with an antiviral effective amount of an antibody of the invention.

It will also be appreciated by one skilled in the art that a DNA sequence encoding a peptide or antibody of the present invention can be introduced into a subject, in order to generate an antibody of the invention (e.g., as a DNA vaccine). Naked DNA can be used; or any of a variety of well-known vectors, such as viral vectors, can be used. Methods of delivery include the methods described above for the introduction of a nucleic acid into a cell, as well as many other conventional methods that will be evident to the skilled worker.

The antiviral agents of the invention can be formulated into various compositions, e.g., pharmaceutical compositions, for use, for example, either in therapeutic treatment methods for infected individuals, or in prophylactic methods against viral infection of uninfected individuals. Generally, a pharmaceutical composition of the invention comprises an antiviral-effective amount of a nucleic acid, peptide or antibody of the invention.

The composition can comprise a carrier, such as a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

A pharmaceutical composition of the invention can contain other pharmaceuticals, in conjunction with the peptide or antibody of the invention, particularly when used to therapeutically treat a viral infection, such as one which results in AIDS. Representative examples of these additional pharmaceuticals include antiviral compounds, virucides, immunomodulators, immunostimulants, antibiotics, absorption enhancers, and agents that inhibit contraception (such as nonoxynol-9). Exemplary antiviral compounds include AZT, ddI, ddC, gancyclovir, acyclovir, fluorinated dideoxynucleosides, non-nucleoside analog compounds, such as nevirapine (Shih et al. (1991), *PNAS* 88, 9878-9882), TIBO derivatives, such as R82913 (White et al. (1991), *Antiviral Res.* 16, 257-266), BI-RJ-70 (Merigan (1991), *Am. J. Med.* 90 (Suppl. 4A), 8S-17S), michellamines (Boyd et al., (1994) *J. Med. Chem.*

37, 1740-1745), calanolides (Kashman et al. (1992), *J. Med. Chem.* 35, 2735-2743), nonoxynol-9, gossypol and derivatives, gramicidin (Bourinbar et al., 1994, supra), and Ro 31-8959. Exemplary immunomodulators and immunostimulants include various interleukins, recombinant sCD4, cytokines (including α-interferon), antibody preparations, blood transfusions, and cell transfusions. Exemplary antibiotics include antifungal agents, antibacterial agents, and anti-*Pneumocystitus carnii* agents. Exemplary absorption enhancers include bile salts and other surfactants, saponins, cyclodextrins, and phospholipids (Davis, 1992, supra).

One skilled in the art will appreciate that the particular formulation will depend, in part, upon the particular inhibitory agent of the invention employed, and the chosen route of administration. Accordingly, there is a wide variety of suitable formulations of the composition of the present invention.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al. (1993), *Science* 260, 912-915).

The inhibitory agents of the invention, alone or in combination with other antiviral compounds, can be made into aerosol formulations to be administered via inhalation. These aerosol formulations can be placed into pressurized acceptable propellants, such as dichlorodifluoromethane, propane, nitrogen and the like.

The inhibitory agent of the invention, alone or in combinations with other antiviral compounds or absorption modulators, can be made into suitable formulations for transdermal application and absorption (Wallace et al., 1993, supra). Transdermal electroporation or iontophoresis also can be used to promote and/or control the systemic delivery of the compounds and/or compositions of the present invention through the skin (e.g., see Theiss et al. (1991), *Meth. Find. Exp. Clin. Pharmacol.* 13, 353-359).

Formulations comprising antibodies which are suitable for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, pessaries, tampons or the like. The formulations may contain, for example, freeze-dried bacteria, such as lactobacilli, that are genetically engineered to directly produce a peptide or antibody of the present invention. Formulations for rectal administration can be presented as a suppository with a suitable base comprising, for example, cocoa butter or a salicylate. Formulations suitable for vaginal administration can be presented as pessaries, tampons, creams, gels, pastes, foams, or spray formulas containing, in addition to the active ingredient. Similarly, the active ingredient can be combined with a lubricant as a coating on a condom. Indeed, preferably, the active ingredient is applied to any contraceptive device, including, but not limited to, a condom, a diaphragm, a cervical cap, a vaginal ring, a dental dam, or a sponge.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

One skilled in the art will appreciate that a suitable or appropriate formulation can be selected, adapted or developed based upon the particular application at hand.

Dosages for an inhibitory agent of the invention can be in unit dosage form, such as a tablet or capsule. The term "unit dosage form" as used herein refers to physically discrete units suitable as unitary dosages for human and animal subjects, each unit containing a predetermined quantity of an antibody of the invention, alone or in combination with other antiviral agents, calculated in an amount sufficient to produce the desired effect in association with a pharmaceutically acceptable diluent, carrier, or vehicle.

The specifications for the unit dosage forms of the present invention depend on the particular inhibitory agent of the invention, or composition thereof, employed and the effect to be achieved, as well as the pharmacodynamics associated with each agent, in the host. In some embodiments, the dose administered is an "antiviral effective amount" or an amount necessary to achieve an "effective level" in the individual patient.

Since the "effective level" is used as the preferred endpoint for dosing, the actual dose and schedule can vary, depending upon individual differences in pharmacokinetics, drug distribution, and metabolism. The "effective level" can be defined, for example, as the blood or tissue level (e.g., about 0.1-1000 nM) desired in the patient that corresponds to a concentration of one or more antibodies of the invention, which inhibits a virus, such as HIV, in an assay known to predict for clinical antiviral activity of chemical compounds and biological agents. The "effective level" for agents of the present invention also can vary when the inhibitory agent of the invention, or composition thereof, is used in combination with AZT or other known antiviral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with surrogate indicators such as p24 or RT) analysis of appropriate patient samples (e.g., blood and/or tissues).

Administration of an inhibitory agent of the invention with other anti-retroviral agents and particularly with known RT inhibitors, such as ddC, AZT, ddI, ddA, or other inhibitors that act against other HIV proteins, such as anti-TAT agents, is expected to inhibit most or all replicative stages of the viral life cycle. The dosages of ddC and AZT used in AIDS or ARC patients have been published. A virustatic range of ddC is generally between about 0.05 nM and about 1.0 nM. A range of about 0.005-0.25 mg/kg body weight is virustatic in most patients. The preliminary dose ranges for oral administration are somewhat broader, for example about 0.001 to about 0.25 mg/kg given in one or more doses at intervals of 2, 4, 6, 8, 12, etc. hours. Currently, about 0.01 mg/kg body weight ddC given every about 8 hrs is preferred. When given in combined therapy, the other antiviral compound, for example, can be given at the same time as the antibody of the invention or the dosing can be staggered as desired. The two drugs also can be combined in a composition. Doses of each can be less when used in combination than when either is used alone.

The dose of an inhibitory agent of the invention, or composition thereof, administered to an animal, particularly a human, in the context of the present invention should be sufficient to effect at least a prophylactic or therapeutic response in the individual over a reasonable time frame. The exact amount of the dose will vary from subject to subject, depending on the species, age, weight and general condition of the subject, the severity or mechanism of any disorder being treated, the particular agent or vehicle used, its mode of administration and the like. The dose used to achieve a desired antiviral concentration in vivo (e.g., about 0.1-1000 nM) will be determined by the potency of the particular inhibitory agent (e.g., antibody) employed, the severity of the disease state of infected individuals, as well as, in the case of systemic administration, the body weight and age of the infected individual. The size of the dose also will be determined by the existence of any adverse side effects that may accompany the particular inhibitory agent (e.g., antibody) of the invention, or composition thereof, employed. It is generally desirable, whenever possible, to keep adverse side effects to a minimum.

For any given formulation or composition comprising an agent of the invention that is attached to or immobilized on a solid support matrix (such as a condom, etc.), the formulation or composition preferably retains the desired (i.e., in this instance, the ability to inhibit viral infection) properties of the inhibitory agent, itself.

Another embodiment of the invention is a kit useful for any of the methods disclosed herein; such a kit comprises one or more isolated peptides, nucleic acids and/or antibodies of the invention. For example, a kit suitable for therapeutic or prophylactic treatment of a virus infection (e.g., an HIV infection) in a subject may further comprise a pharmaceutically acceptable carrier and, optionally, a container or packaging material. Among other uses, kits of the invention can be used in experiments to study mechanisms by which CCR5-mediated infection by HIV is accomplished. A skilled worker will recognize components of kits suitable for carrying out any of the methods of the invention.

Optionally, the kits comprise instructions for performing the method. Kits of the invention may further comprise a support or matrix to which peptides or antibodies of the invention can be attached or immobilized. Other optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form.

In the foregoing and in the following examples, all temperatures are set forth in uncorrected degrees Celsius; and, unless otherwise indicated, all parts and percentages are by weight.

EXAMPLES

Example I

Material and Methods

A. Materials. A random linear dodecapeptide phage display library (Ph.D-12), wherein the displayed peptide (12-mer) is expressed fused to the N-terminus of gIII protein was purchased from New England Biolabs (Beverly, Mass.). Monoclonal antibody (mAb) 2D7 was purchased from BD Pharmingen (San Diego, Calif.). Immunoglobulin and HRP (horseradish peroxidase) conjugated secondary antibodies used for ELISA were obtained from Jackson Immuno Research Laboratories (West Grove, Pa.). Buffers and substrates for ELISA were purchased from KPL Biotech (Gaithersburg, Md.). New Zealand Rabbits were procured from Charles River (Wilmington, Mass.).

B. Epitope mapping using phage display library. A random, linear, dodecapeptide-phage display library (Ph.D-12, New England Biolabs) was used for mAb 2D7 epitope mapping. Affinity selection of the phage clones from the random peptide library was carried out per the manufacturer's instructions with minor modifications. Microtiter wells were coated with 200 ng mAb 2D7 in 100 µl PBS, pH 7.4, at 4° C. for 12 h followed by 1 h at room temperature (RT). The wells were washed with PBS containing 0.05% Tween-20 (PBST) and blocked with EMEM containing 5% FBS at RT for 2 h. The phage library ($1 \times 10^{10}$ phages/100 µl) was added to the blocked wells and incubated at RT for 1 h. Unbound phages were washed-off with ten washes of PBST followed by three washes with PBS. The bound phages were eluted at low pH by incubation with elution buffer (0.1 N Gly.HCl, pH 2.2 containing 1 mg/ml BSA) at 37° C. for 10 min. Eluent phages were neutralised with 6 µl of 2 M Tris (pH unadjusted) per 100 µl phage eluate. After four rounds of biopanning, the phage clones were analysed by DNA sequencing and affinity-capture phage ELISA.

C. Phage ELISA. Phages used for ELISA were derived from clones selected after the fourth round of panning. Microtiter plates coated with 200 ng of mAb 2D7 were blocked with EMEM containing 5% FBS (blocking solution). The phages ($10^{10}$/100 µl/well) diluted in blocking solution were then added and incubated for 1 h at room temperature (RT). The plates were washed three times with PBST prior to addition of HRP-conjugated anti-phage antibody (GE Healthcare, Piscataway, N.J.), and the reaction was quantified using ABTS substrate. Absorbance was measured at 405 nm.

D. Peptide ELISA. Peptides were biotinylated using melamine PEO2-Biotin reagent as per manufacturer's instructions (Pierce Biotech, Rockford, Ill.). The biotinylated peptide (1 µg/well) was captured onto wells coated with 200 ng of streptavidin. After blocking with EMEM containing 5% FBS, serial dilutions of mAb 2D7 in blocking solution were added to each well, incubated for 1 hr at RT, followed by addition of peroxidase-conjugated goat anti-mouse IgG. The reaction was quantified using ABTS substrate. Absorbance was measured at 405 nm. The synthetic peptides that were used in the study are outlined in Table 1.

TABLE 1

Sequences of peptides used in the study

| PEPTIDE IDENTITY | PEPTIDE SEQUENCE | |
|---|---|---|
| 2D7-2SK | E-W-Q-K-E-G-L-V-T-<br>L-W-L-G-G-G-G-S-C | (SEQ ID NO: 4) |
| 2D7-2SK-T9A | E-W-Q-K-E-G-L-A-<br>L-W-L-G-G-G-G-S-C | (SEQ ID NO: 5) |
| 2D7-2SK-L10A | E-W-Q-K-E-G-L-V-T-<br>A-W-L-G-G-G-G-S-C | (SEQ ID NO: 6) |
| 2D7-2SK-T9A,L10A | E-W-Q-K-E-G-L-V-A-<br>A-W-L-G-G-G-G-S-C | (SEQ ID NO: 7) |
| 2D7-2SK-K4R | E-W-Q-R-E-G-L-V-T-<br>L-W-L-G-G-G-G-S-C | (SEQ ID NO: 8) |
| 2D7-2SK-SCR | Q-L-W-L-G-W-T-E-L-<br>E-G-V-K-G-G-S-C | (SEQ ID NO: 9) |
| M23 | F-C-A-L-D-G-D-F-G-<br>W-L-A-P-A-C | (SEQ ID NO: 10) |

E. Competition phage ELISA using synthetic peptides. Competition of peptides with selected phage clones for binding to mAb 2D7 was performed by phage ELISA. Synthetic 2D7-2SK peptide (or its biotinylated derivative), or a control peptide (CGRAARIGFPGAYTTKNG) (SEQ ID NO:3), were added to mAb 2D7-coated wells for 30 min at RT. The phages ($10^9$/100 µl/well) were added to mAb 2D7-coated wells, which were pre-incubated in the absence or presence of various concentrations of competing peptides. The reaction was developed as described for phage ELISA.

F. Cell-ELISA. The Cf2Th canine cell line and the hCCR5-transfected Cf2Th/synCCR5 derivative were obtained through the AIDS Research and Reference Reagent Program (Cat #4662, contributed by Drs. Tajib Mirzabekov and Joseph Sodroski (Mirzabekov et al. (1999) *J Biol Chem* 244, 28745-50), McKesson HBOC BioServices, Rockville, Md.). Forty eight hours before the ELISA, 200 µl of $10^5$ cells/ml were plated in 96-well plates and incubated at 5% $CO_2$, 37° C. The plates were gently washed with Dulbecco's PBS supplemented with $Ca^{2+}$ and $Mg^{2+}$ after each incubation step during ELISA. Serial dilutions of control or anti-CCR5 antibodies in EMEM containing 5% FBS were added to each well followed by addition of peroxidase-conjugated goat anti-mouse or anti-rabbit IgG. The reaction was quantified using ABTS substrate. Absorbance was measured at 405 nm.

G. Flow cytometry. CEM. NKR.CCR5 (a generous gift from John Moore, Rockefeller University) were stained with 10 µg/ml mAb 2D7 (or isotype matched control mouse IgG), or with 25 µg/ml rabbit anti-2D7-2SK IgG (or with pre-immune rabbit IgG) for 60 min on ice, followed by extensive washing and staining with FITC-Goat anti-mouse or with FITC Goat anti-rabbit antibodies (Sigma). Flow cytometry was performed and analyzed with Cell Quest Software on FACSCalibur (BD Biosciences).

H. Rabbit immunization and antibody purification. New Zealand rabbits were immunized sub-cutaneously with 500 µg of KLH-conjugated peptide emulsified in Complete Freund's adjuvant (CFA). Two booster doses at 21-day intervals, with 500 µg antigen emulsified in Incomplete Freund's adjuvant (IFA) were injected subcutaneously. The rabbits were bled after 8 days of the second boost, and the isolated serum was titered for peptide binding by ELISA. The polyclonal rabbit IgG was affinity purified on a peptide-coupled gel using a sulfolink kit (Pierce Biotech, Rockford, Ill.).

I. Affinity Measurements by Biacore. Steady-state equilibrium binding of mAb 2D7 and rabbit antibodies raised against the 2D7-2SK peptide was monitored at 25° C. using a Biacore 3000 surface plasmon resonance biosensor (Biacore AB, Uppsala, Sweden). The 2D7-2SK peptide was coupled to a F1 sensor chip using sulfhydryl coupling with 60 resonance units (RU), 120 RU, 400 RU in the three test flow cells. One hundred microliter samples of freshly prepared antibody at various concentrations were injected at a flow rate of 25 µl/min (240 second contact time). Flow was directed over a mock surface to which no protein was bound, followed by the 2D7-2SK peptide-coupled-surface. Responses from the peptide surface were corrected for the response from the mock surface and for responses from a separate, buffer only, injection. Binding surfaces in the flow cells were regenerated by the injection of two 30-second injections of 10 mM Glycine at pH 2.5. All injections were done three times. Rabbit anti-anthrax protective antigen or anti-ovalbumin antibodies were used as control non-specific antibodies in various binding experiments.

For the competition experiments, various concentrations of rabbit anti-2D7-2SK peptide (diluted with non-immune rabbit IgG so that rabbit immunoglobulin concentration was constant) were mixed 1:1 with mAb 2D7 at a concentration of 12.5 µg/ml, and 25 µl samples were injected at a flow rate of 10 µl/min through 2D7-2SK peptide-coated chips. In these experiments, mAb 2D7 specific binding in presence of rabbit antibodies was quantified by injection of 25 µl of goat anti-mouse IgG (25 µg/ml). The experimental conditions were identical in the reverse competition analysis of the rabbit anti-2D7-2SK binding to 2D7-2SK peptide in the presence of mAb 2D7. In that case, mAb 2D7 was diluted with non-immune mouse IgG, so that mouse immunoglobulin concentration was kept constant. Bound rabbit antibodies were quantified by a goat anti-rabbit IgG antibody (25 µg/ml) to determine the association of rabbit anti-2D7-2SK to the 2D7-2SK peptide-coated chip in the presence of increasing concentrations of mAb 2D7.

J. Fusion-inhibition assays. The $CD4^-$ T cell line 12E1, was infected with HIV-1 envelope-expressing recombinant vaccinia viruses at 10 PFU/cell overnight. Envelope-expressing 12E1 cells or TF228 (stably transfected cells expressing IIIB/BH10 envelope) were mixed (1:1) with the human PM1 cell line (a $CD4^+$ $CXCR4^+CCR5^+$ derivative of the Hut 78 cell line that is susceptible to infection by both X4 and R5 strains, or with PHA/IL2-activated Rhesus PBMC. Various antibodies were added at different concentrations to these target cells and incubated for 1 h at 37° C. The envelope-expressing 12E1 effector cells were then added (at 1:1 effector/target ratio) as previously described (Golding et al. (2002) *J Virol* 76, 6780-90). The numbers of multinucleated syncytia were scored at various times after initiation of co-cultures. Peak syncytium-formation was usually observed between 3 and 5 h). All groups were plated at two or three replicates, and all experiments were done at least three times.

K. HIV-1 strains and virus neutralization assays. HIV-1 strains IIIB (X4 virus) and BaL, JR-CSF or primary isolate 92US657 (R5 viruses) were obtained from the AIDS Research and Reference Reagent Program (McKesson HBOC BioServices, Rockville, Md.). Viral stocks were propagated and their titers were determined in phytohemag-glutinin-activated (PHA) peripheral blood mononuclear cells (PBMC). The CCR5-expressing PM1 cells or human PBMCs ($2.5 \times 10^4$ cells/well, in 96-well plates) were pre-incubated with the different antibodies (two-fold dilutions, starting at 50

µg/ml final concentration) for 120 min at 37° C., followed by addition of viruses at 50 $TCID_{50}$/well (five replicates per group). The plates were washed extensively after 24 h to remove residual virions and antibodies. Every second day thereafter, the supernatants were removed and the cultures were supplemented with fresh medium (without inhibitors). Virus production was determined by measuring p24 in the supernatants with ELISA kit (NEN Life Sciences Products Inc., Boston, Mass.). Virus neutralization by the different antibodies is expressed either as percent inhibition of p24 production at a given concentration.

Example II

Figure 8:
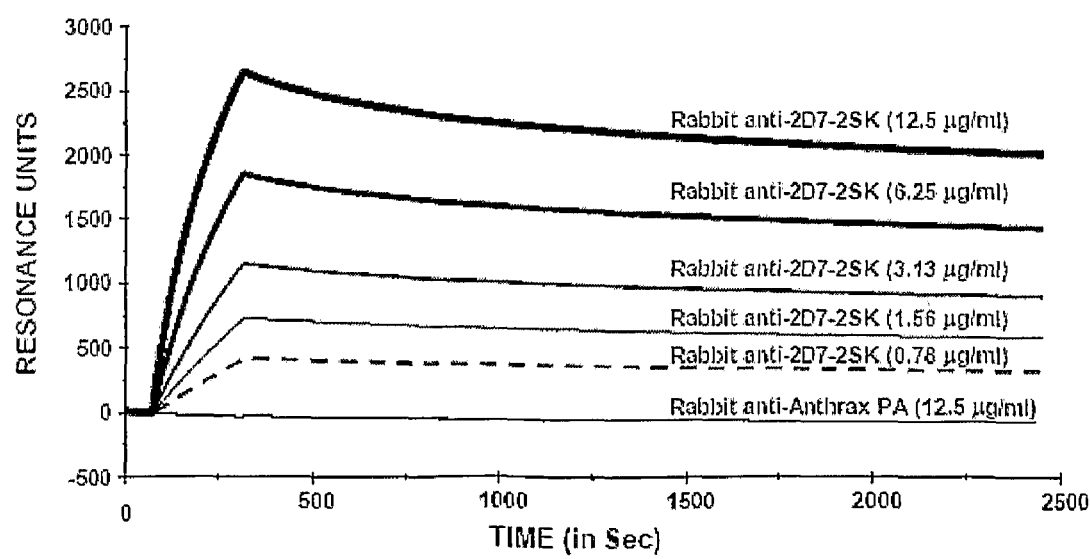
Figure 9:
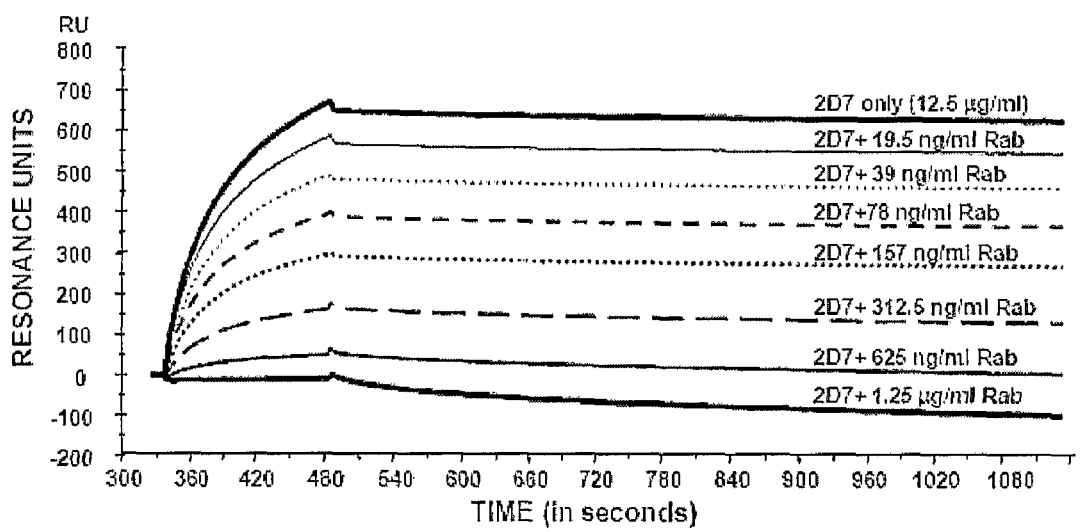
Figure 9:
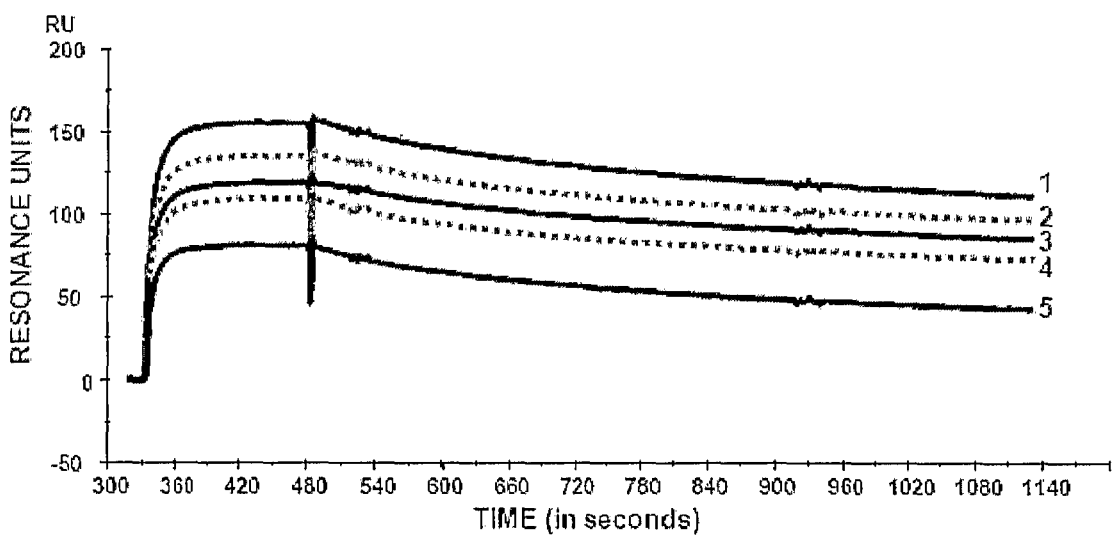

Identification of a Linear Peptide Recognized by Monoclonal Antibody 2D7 Capable of Generating CCR5-Specific Antibodies with HIV Neutralizing Activity A. mAb 2D7 Recognizes a Linear Peptide Containing Two Distant Sequences in the ECL-2 of Human CCR5.

The 2D7 mAb is one of the murine monoclonal antibodies demonstrating a potent inhibition of HIV-1 cell entry. This mAb recognizes an epitope in the first half of ECL-2, which is affected by local conformation and may involve several non-linear regions. Our goal was to identify a linear peptide that binds with high affinity to mAb 2D7 and can be used as an immunogen to elicit 2D7-like antibodies in other species. For that purpose we used a random dodecamer peptide phage-display library to perform biopanning in microtiter wells coated with mAb 2D7. Four rounds of affinity selection led to the isolation of phage clones that showed strong specific reactivity to mAb 2D7 in phage ELISA (FIG. 1). Sequencing of the DNA inserts in four 2D7-binding phages revealed identical sequences with a deduced amino acid sequence E-W-Q-K-E-G-L-V-T-L-W-L (SEQ ID NO:1). Alignment of this peptide with the human CCR5 sequence (Lee et al. (1999) *J Biol Chem* 274, 9617-26; Samson et al. (1996) *Genomics* 36, 522-6) revealed homologies to two distal regions in the ECL-2 of human CCR5 molecule. One located in the amino-terminus of ECL-2 (170-QKEGL-174) (SEQ ID NO:2) and the second one at the carboxy terminus of the ECL-2 (195-TL-196) (FIG. 2). The identified peptide insert, termed 2D7-2SK, was chemically synthesized and was used in subsequent binding and functional assays.

In ELISA, mAb 2D7 showed a concentration-dependent specific reactivity with biotinylated 2D7-2SK peptide (but not with biotinylated scrambled 2D7-2SK peptide) captured by streptavidin (FIG. 3A). Furthermore, binding of phage p2D7-2SK to mAb 2D7-coated plates was inhibited by free 2D7-2SK peptide, but not by a control peptide, in a dose dependent manner (FIG. 3B).

The first region of homology with CCR5 includes three amino acids that were previously shown to play a critical role in mAb 2D7 binding [170-QKE-172, (Olsen et al. (1999) *J Virol* 73, 4145-55)]. However, the two amino acids in the 3' part of ECL-2 had not been implicated in mAb 2D7 binding. To address their role in the binding of the mAb to the linear peptide, either Thr, Leu, or both were substituted by alanines. All the alanine substitutions completely abolished binding of mAb 2D7 to the 2D7-2SK peptide in ELISA (FIG. 3C), thus establishing the crucial role played by these amino acids in this peptide for 2D7 binding. The importance of previously reported Lys-171 residue for mAb 2D7 binding was also confirmed in our peptide ELISA, wherein mAb 2D7 completely lost binding to a 2D7-2SK derivative (2D7-2SK-K4R, Table 1) containing a lysine to arginine substitution at the fourth position of 2D7-2SK peptide. In these experiments, the amounts of different 2D7-2SK peptide derivatives captured by the streptavidin-coated wells were found to be equivalent as determined by the similar reactivity of rabbit polyclonal antibodies generated against the 2D7-2SK peptide.

Binding affinity of mAb 2D7 for the 2D7-2SK peptide was determined using surface plasmon resonance analysis in a Biacore system (FIG. 4). The pattern of binding to peptide-coated chips was typical of bivalent antibody molecules. The affinity constant for the binding of mAb 2D7 to 2D7-2SK peptide thus calculated was 0.18 nM.

B. Binding of Peptide 2D7-2SK to mAb 2D7 Blocks its Viral Fusion Inhibition Activity.

If the linear peptide 2D7-2SK mimics the epitope in the native CCR5 co-receptor recognized by mAb 2D7, then binding of the peptide should interfere with the ability of mAb 2D7 to block HIV-1 envelope-mediated cell fusion. As can be seen in FIG. 5, mAb 2D7 (at 1 μg/ml) blocked fusion between PM1 ($CD4^+$/$CCR5^+$) cells and 12E1 ($CD4^-$) cells expressing JR-FL envelope by 60%, as measured in our syncytium-formation assay. The 2D7-2SK peptide by itself did not demonstrate any inhibitory activity in the fusion assay (not shown). Preincubation of mAb 2D7 with 2D7-2SK peptide (either biotinylated or non-biotinylated) resulted in significant reduction of its fusion inhibiting activity. Similar results were obtained with 12E1 cells expressing the BaL envelope. In contrast, a previously reported mimitope sequence for mAb 2D7 identified using phage display library (MD23) that contains no homology to CCR5 sequence (Meta et al. (1999) *Mol Immunol* 36, 1249-54) did not bind to mAb 2D7, and also did not block the fusion inhibiting activity of mAb 2D7 (FIG. 5).

C. 2D7-2SK Peptide can Elicit Polyclonal Antibodies with 2D7-Like Specificity in Rabbits.

Since 2D7-2SK peptide bound with high affinity to mAb 2D7 and reversed its anti-viral activity, it was predicted that this linear peptide acquires a conformation that resembles the epitope recognized by mAb 2D7 in the native form of human CCR5 molecule. To test this hypothesis, we determined if this peptide can be used as an immunogen to elicit 2D7-like antibodies in animals. To that end, white New Zealand rabbits were immunized thrice with KLH conjugated 2D7-2SK peptide, and the IgG fraction of the hyper-immune sera was tested in binding assays. The 2D7-2SK specific antibodies bound in a concentration-dependent fashion to biotinylated 2D7-2SK peptide, captured on streptavidin-coated wells in ELISA (FIG. 6A). No reactivity with control streptavidin-coated wells, or biotinylated-BSA captured by streptavidin, was observed, and the pre-immune rabbit serum did not react with any of the peptide-coated plates. To check whether these rabbit anti-2D7-2SK peptide antibodies recognize native CCR5 molecules expressed on the cell surface, a cell-ELISA was performed using the stably transfected $CCR5^+$ Cf2Th cell line. The rabbit anti-2D7-2SK antibodies bound $CCR5^+$ Cf2Th cells, but only minimally to the $CCR5^-$ parental Cf2Th cell line (FIG. 6B). To further confirm the specificity of these rabbit anti-2D7-2SK antibodies to the cell surface native CCR5 molecule, flow cytometry was performed that showed us specific staining of only CCR5 expressing CEM cells by Rabbit anti-2D7-2SK antibodies and not by pre-immunized rabbit IgG (FIG. 7). No staining was observed for control CEM cells (not expressing CCR5) with the rabbit anti-2D7-2SK antibodies.

In surface plasmon resonance analysis, the rabbit anti-2D7-2SK antibodies displayed antigen-specific and concentration-dependent binding kinetics to 2D7-2SK peptide. The observed pattern is typical of polyclonal antibodies. The fast on-rate, strong binding and very slow off-rate suggest that the rabbit polyclonal IgG contain antibodies with high affinity for 2D7-2SK peptide (FIG. 8). Furthermore, the rabbit antibodies competed with mAb 2D7 for binding to the 2D7-2SK peptide coupled to Biacore CM5 chip (FIG. 9A). This competition was very effective as even at 10-fold lower concentration of the rabbit anti-2D7-2SK antibodies (1.25 µg/ml) blocked binding of mAb 2D7 binding (at 12.5 µg/ml) to the 2D7-2SK peptide (FIG. 9A; lowest curve). In a corresponding reverse competitive Biacore analysis, even a 20-fold excess of mAb 2D7 (Rabbit IgG+250 µg/ml 2D7) was unable to completely block the binding of rabbit anti-2D7-2SK antibodies to the 2D7-2SK peptide-coupled chip (FIG. 9B).

D. Blocking of HIV Fusion and Infectivity by Rabbit Anti-2D7-2SK Peptide Antibodies.

Figure 10:
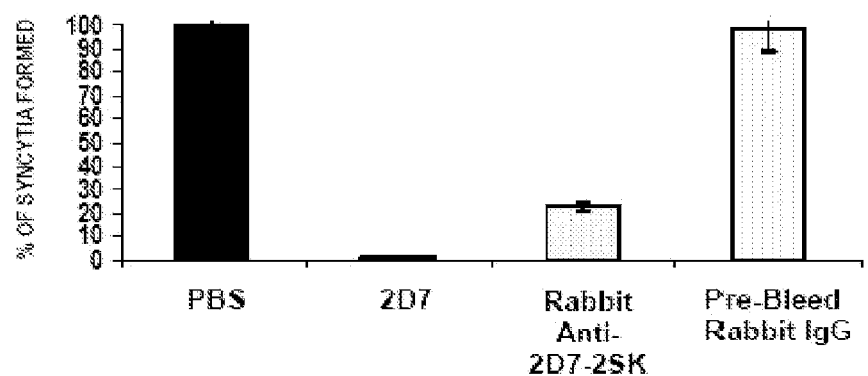
Figure 10:
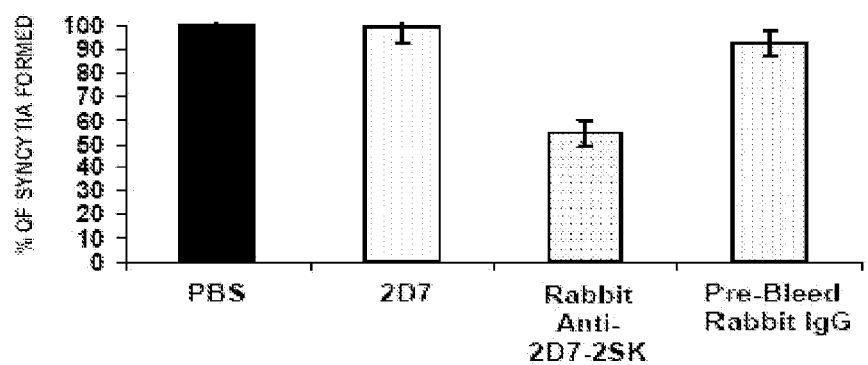

As similar binding specificities were observed for mAb 2D7 and the rabbit anti-2D7-2SK peptide antibodies, it was important to determine if they also share the ability to inhibit fusion between R5 HIV-1 envelope-expressing effector cells and CD4$^+$ CCR5$^+$ target cells. As depicted in FIG. 10A, while mAb 2D7 caused 98% fusion inhibition at 10 µg/ml, 77% inhibition was observed for an equivalent concentration of the polyclonal rabbit anti-2D7-2SK antibodies. Similar results were obtained using 12E1 expressing HIV-1 envelopes derived either from BaL or JR-FL strains.

Figure 3:
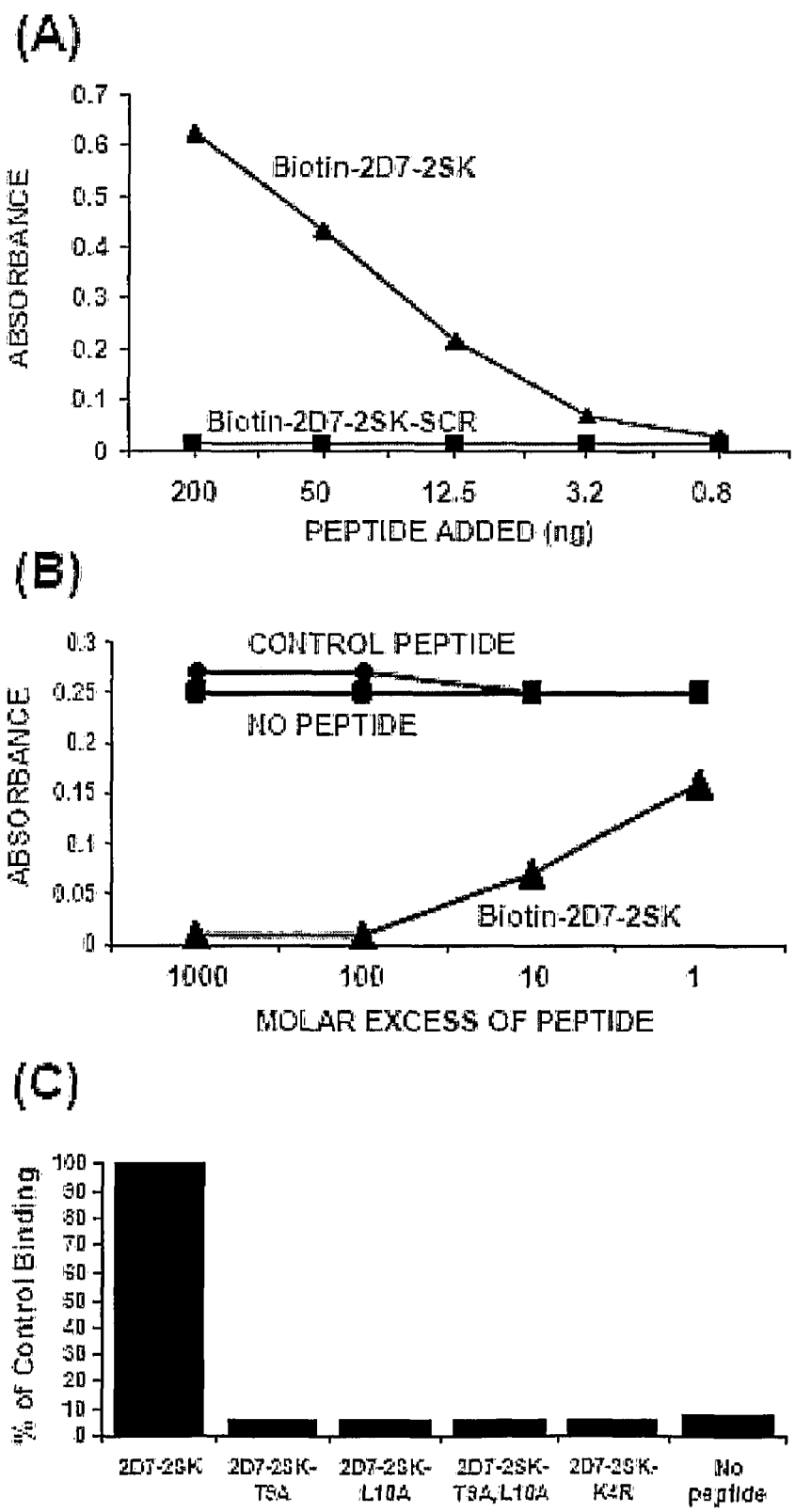
Figure 4:
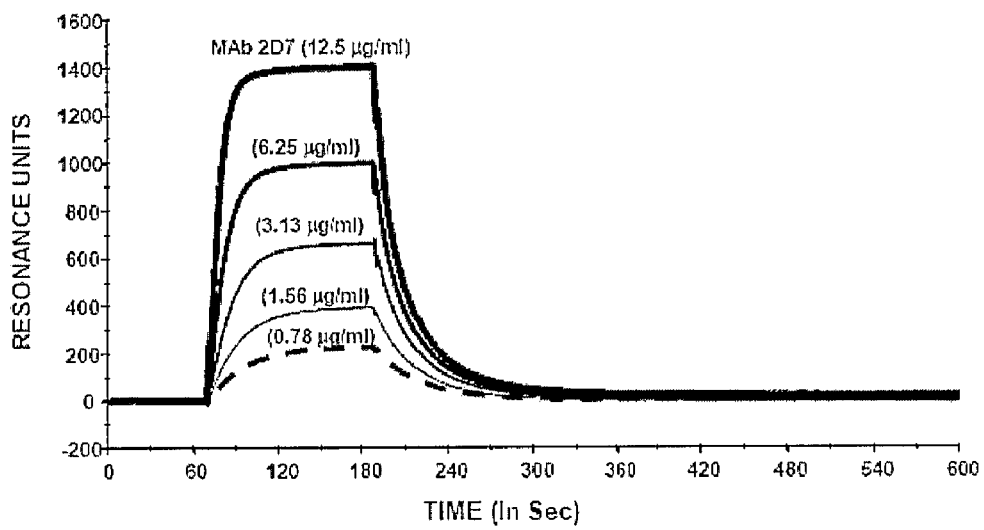
Figure 5:
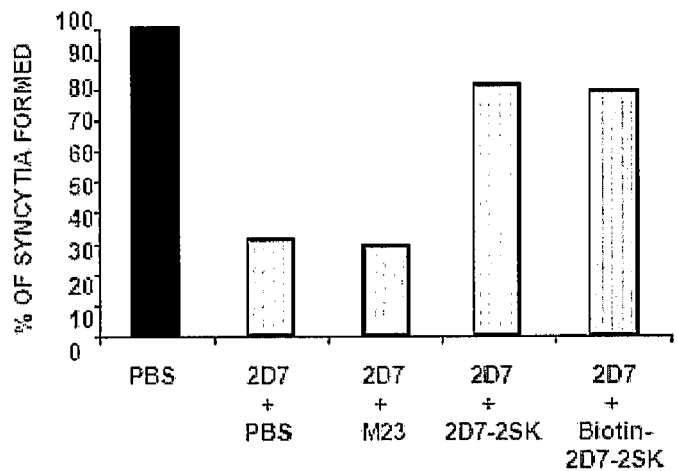
Figure 6:
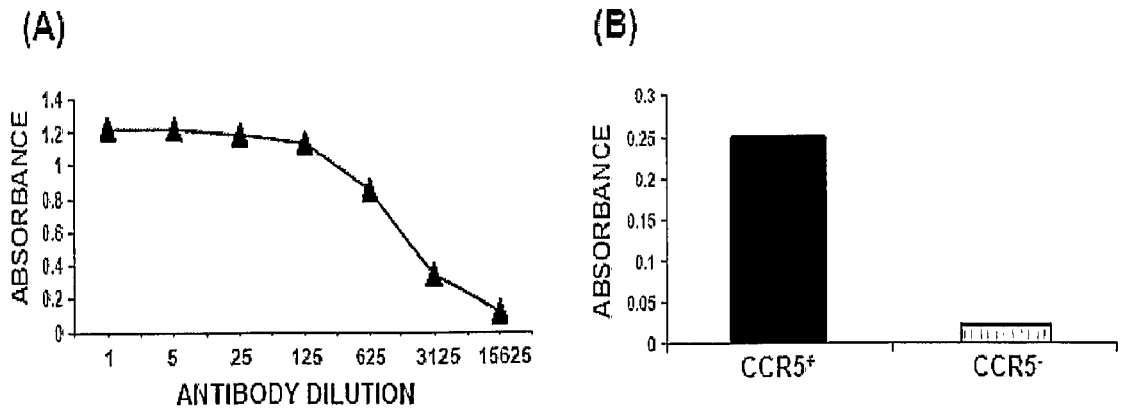
Figure 7:
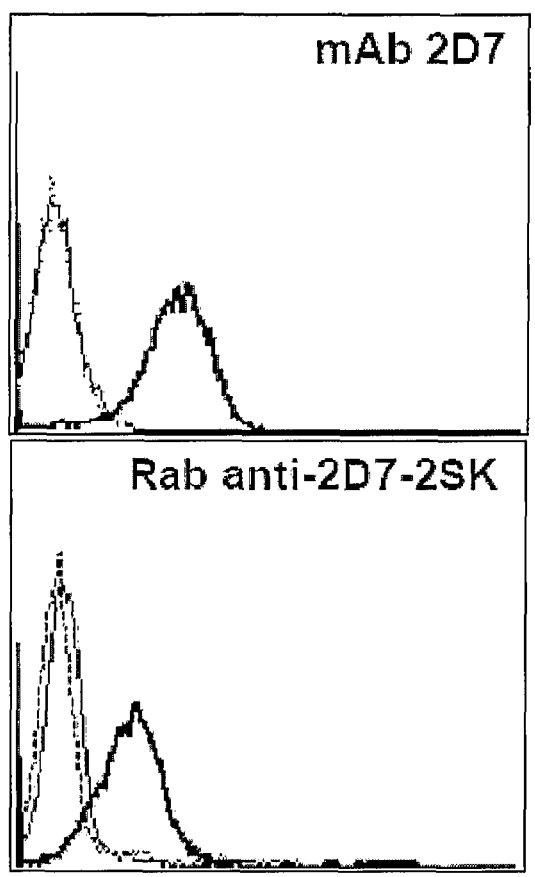

It was previously reported that mAb 2D7 does not interact with rhesus CCR5 and does not block SIV infection. This was attributed to a single substitution (K171R) within the mAb 2D7 putative epitope in Rhesus CCR5 (Siciliano et al. (1999) *J Biol Chem* 274, 1905-13). The importance of this mutation in mAb 2D7 epitope was confirmed in our peptide ELISA, as mAb 2D7 completely lost binding to a 2D7-2SK derivative (2D7-2SK-K4R, FIG. 3C) containing a lysine to arginine substitution at the fourth position of 2D7-2SK peptide (Table 1). In further agreement with the above finding, nab 2D7 did not inhibit syncretism formation between of SIV env-expressing cells and the Rhesus PBMCs (FIG. 10B). Surprisingly, the rabbit anti-2D7-2SK antibodies showed a moderate but specific inhibition of Rhesus PBMC fusion with 12E1 expressing SIV envelope (derived either from SIV$_{239}$ or SIV$_{316}$), suggesting that a fraction of the polyclonal antibodies recognize CCR5 epitopes that are conserved between human and Rhesus CCR5 molecules. Their binding is not entirely dependent on lysine-171, which is crucial for 2D7 binding.

Figure 11:
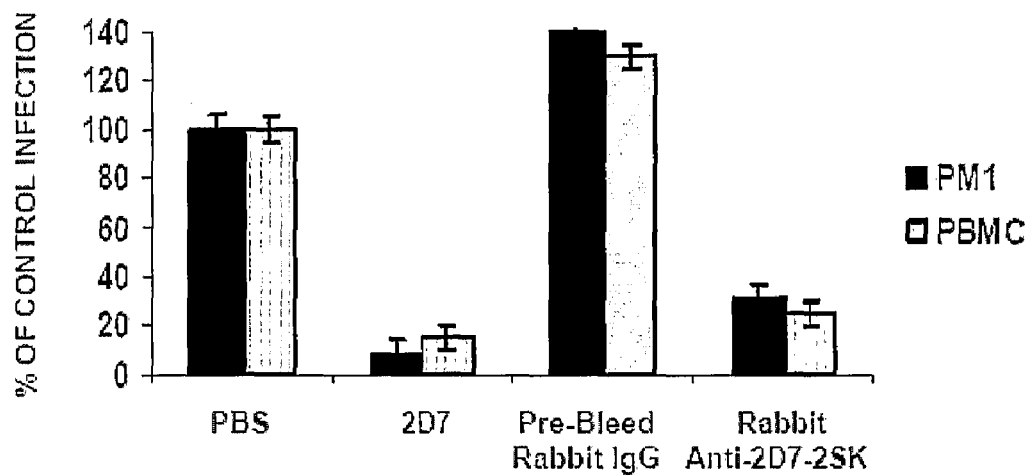
Figure 11:
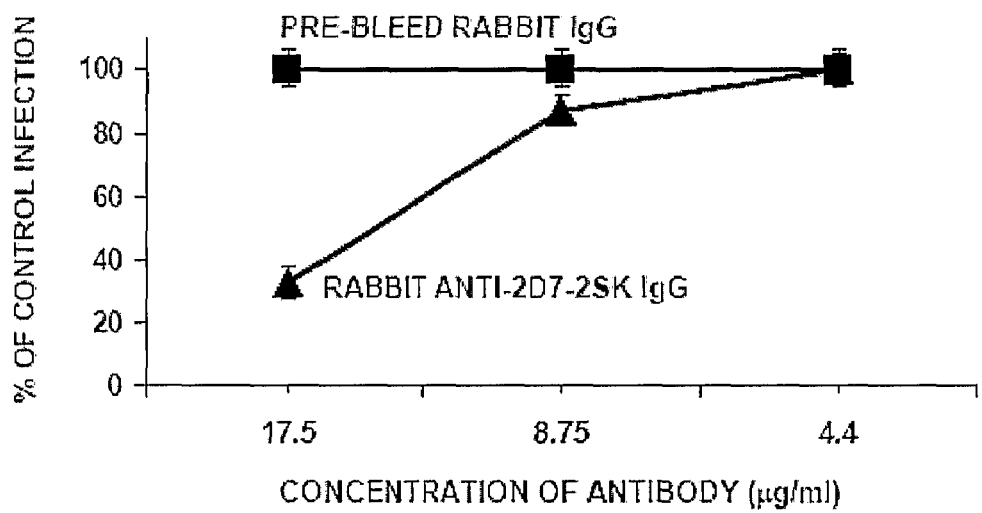

The activity of the rabbit antibodies was further evaluated in cell-free viral infection assays with either PM1 or human PBMC target cells. Using either HIV-1 BaL or JR-CSF R5 viruses (but not X4 virus), significant reduction in p24 was observed in the presence of either mAb 2D7 or rabbit anti-2D7-2SK antibodies at 50 µg/ml final concentration (FIG. 11A). This inhibition of virus entry by rabbit anti-2D7-2SK peptide antibodies was specific, as control rabbit IgGs at similar antibody concentration did not show any decrease in HIV-1 infection. The CCR5-tropic virus neutralization by polyclonal rabbit anti-2D7-2SK antibodies (72-80%) was comparatively lower than that observed for equivalent amount of 2D7 monoclonal antibody (82-93%) in multiple experiments. Dose-dependent dilution studies in PBMC infectivity experiments with the purified rabbit anti-2D7-2SK antibodies were performed using BaL, JR-CSF and primary isolate 92US657 (FIG. 11B; data shown for 92US657). The calculated IC$_{50}$ values were between 10-20 µg/ml for all the viruses tested. This is in comparison to IC$_{50}$ value of 2-4 µg/ml observed with mAb 2D7 observed for these isolates in these experiments.

Together these data suggest that the linear 12-mer peptide, which was identified by affinity selection of random peptide phage-display library on immobilized mAb 2D7, behaves similar to the CCR5 conformational epitope recognized by this potent monoclonal antibody. Furthermore, this peptide mimitope is capable of eliciting 2D7-like HIV-1 neutralizing antibodies in rabbits.

Example III

Isolation and Characterization of Single-Chain Human Mabs and Full Size Human Antibodies Against the Peptide 2D7-2SK The 2D7-2SK peptide was used to screen a highly diverse recombinant synthetic human ScFv (single chain) IgG library (from Itai Benhar, University of Tel-Aviv). Eleven antibodies were isolated and characterized.

Figure 12:
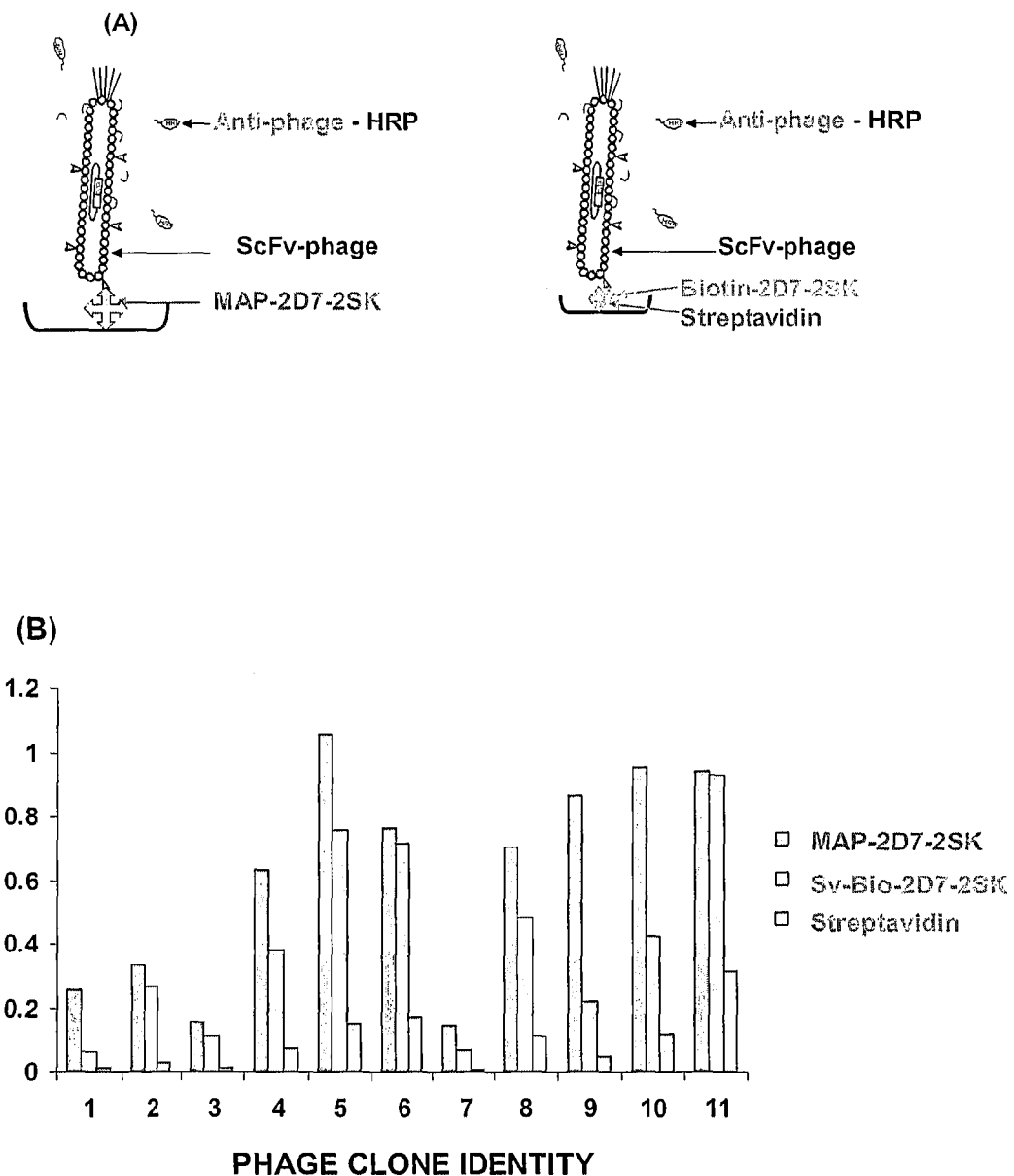
Figure 13:
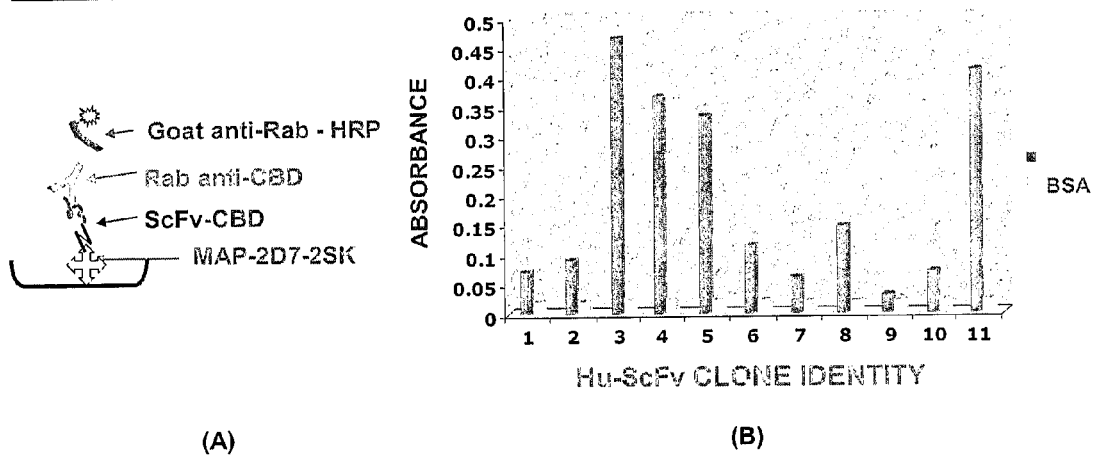
Figure 14:
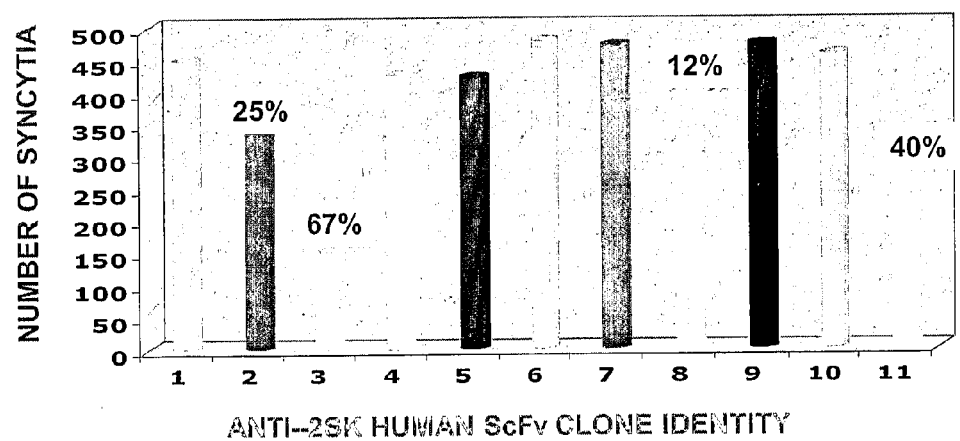
Figure 15:
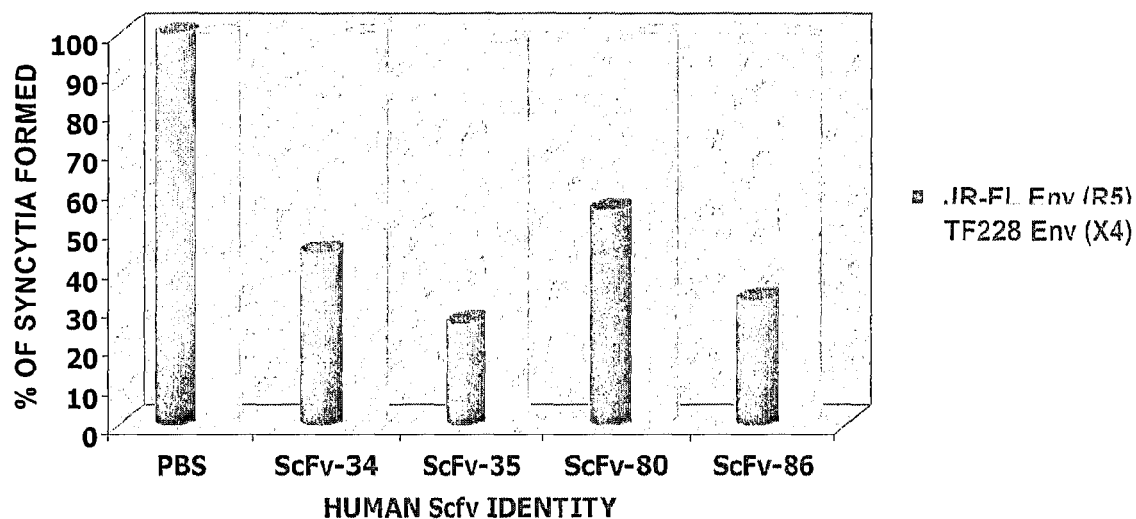
Figure 16:
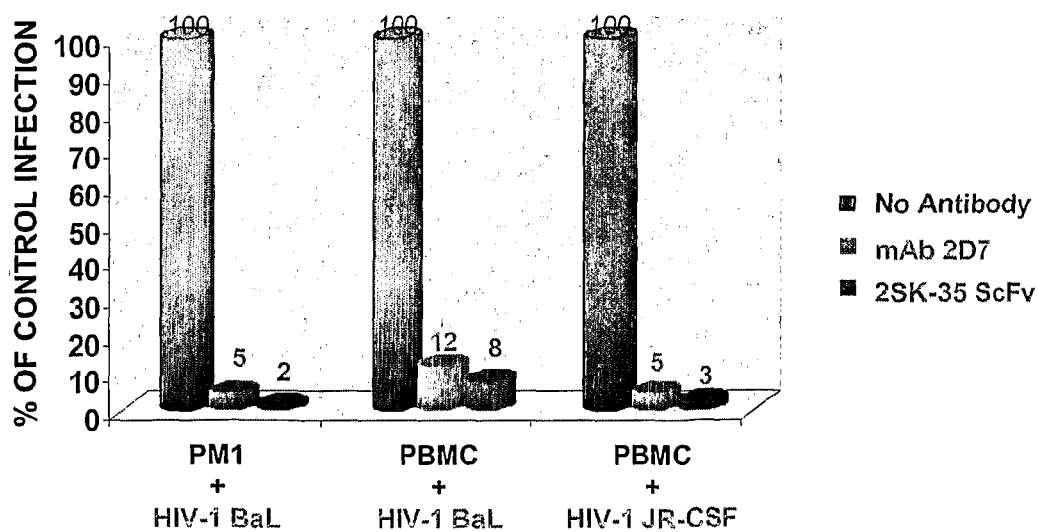
Figure 17:
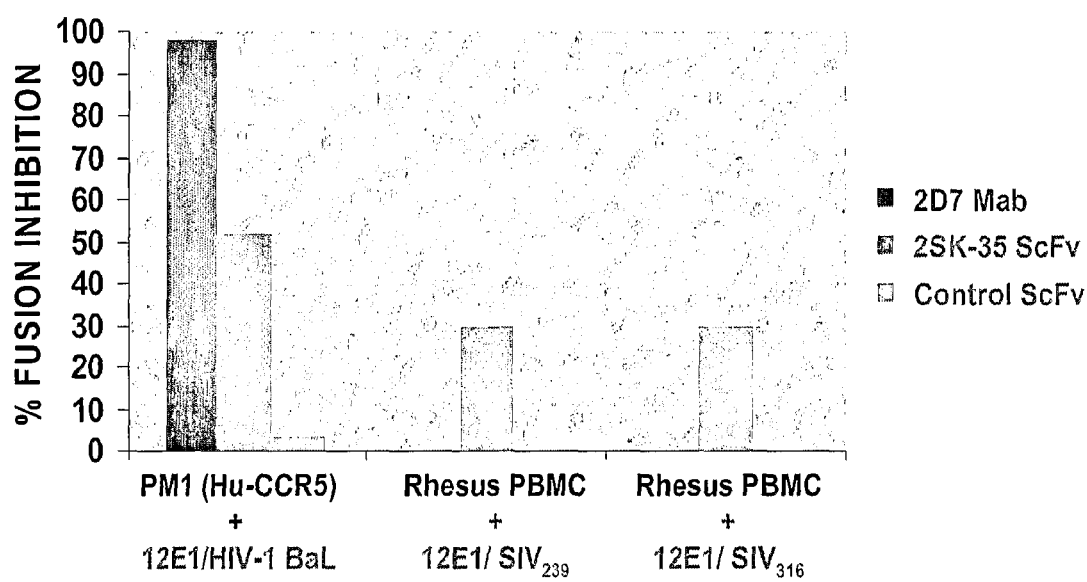
FIG. 17 shows that SK-35 ScFv inhibits syncytia formation by SIV envelopes with Rhesus CCR5 expressing cells.

The results of a typical binding assay of the eleven candidate ScFv's to the 2D7-2SK peptide are shown in FIG. 12. Binding in ELISA is shown in FIG. 13. Inhibition of HIV syncytia formation is shown in FIG. 14. FIG. 15 shows that the four most promising antibodies demonstrate the same specificity of fusion inhibition as the polyclonal rabbit antibodies and mouse mAb 2D7. Two of these antibodies exhibited particularly desirable properties and were selected for further studies. Those two antibodies are ScFv-2SK-34 (sometimes referred to herein as SK-34) and ScFv-2SK-35 (sometimes referred to herein as SK-35). FIG. 16 shows that human ScFv-anti-2SK-35 inhibits HIV-1 in infection assays. FIG. 17 shows that SK-35 inhibits syncytia formation by SIV envelopes with Rhesus CCR5 expressing cells.

The VH and VL regions of ScFv-2SK-34, ScFv-2SK-35, ScFv-2SK-80 and ScFv-2SK-86 (see FIG. 15) were sequenced.

VH (Heavy Chain Variable region) nucleotide sequence of 2SK-34 ScFv (SEQ ID NO: 11)
5'GAGGTGCAGCTGTTGGAGTCTGGGGGAGGCTTGGTACAGCCTGGGGGG TCCCTGAGACTCTCCTGTGCAGCCTCTGGATTCACCTTTGAtGATTATGG

AATGAGCTGGGTCCGCCAGGCTCCAGGGAAGGGGCTGGAGTGGGTCTCAG

TTATTAGTGCTAGTGGTGGTAGCACATACTACGCAGACTCCGTGAATGGC

CGGTTCACCATCTCCAGAGACAATTCCAAGAACACGCTGTATCTGCAAAT

GAACAGCCTGAGAGCCGAGGACACGGCCGTGTATTACTGTGCAAGATACT

TGCCTGGTCTTTGGGCTATGGACGTCTGGGGCCAGGGCACCCTGGTCACA

GTCTCTTCAGGCTCAGCA-3'

VH (Heavy Chain Variable region) protein sequence of 2SK-34 ScFv (SEQ ID NO: 12)
NH$_2$EVQLLESGGGLVQPGGSLRLSCAASGFTFDDYGMSWVRQAPGKGLEW

VSVISASGGSTYYADSVNGRFTISRDNSKNTLYLQMNSLRAEDTAVYYCA

RYLPGLWAMDVWGQGTLVTVSSGSA-COOH

VL (Light Chain Variable region) nucleotide
sequence of 2SK-34 ScFv (SEQ ID NO: 13)
5'GATATCGTGCTGACTCAGCCACCCTCAGCGTCTGGGACCCCCGGGCAG

AGGGTCACCATCTCTTGTACCGGAAGCAGATCCAACATTGGGAAGAATTA

TGTTTCCTGGTACCAGCAGCTTCCAGGAAAGGCTCCCAAACTCCTCATCT

ATAAGAATTATCAGCGGCCCTCAGGGGTCCCTGACCGGTTCTCTGGCTCC

AAGTCTGGCACCTGAGCCTCCCTGGCCATCAGTGGGCTGCGGTCCGAGGA

TGAGGCTGATTATTACTGTGCAGCATGGGATGACAGTCTGAGTGGTTGGG

TGTTCGGCGGAAGCACCCAGCTCACCGTCCTCGCG-3'

VL (Light Chain Variable region) protein sequence
of 2SK-34 ScFv (SEQ ID NO: 14)
NH2DIVLTQPPSASGTPGQRVTISCTGSRSNIGKNYVSWYQQLPGKAPKL

LIYKNYQRPSGVPDRFSGSKSGTSASLAISGLRSEDEADYYCAAWDDSLS

GWVFGGSTQLTVLA-COOH

VH (Heavy Chain Variable region) nucleotide
sequence of 2SK-35 ScFv (SEQ ID NO: 15)
5'GAGGTGcaGCTGTTGGAGACTGGGGGAGGCTTGGTACAGCCTGGGGGG

TCCCTGAGACTCTCCTGTGCAGCCTCTGGATTCACCTTCAGTGACTATTA

CATGAGCTGGGTCCGCCAGGCTCCAGGGAAGGGGCTGGAGTGGGTTTCAG

GACTGAGTGGTTTTGGTCGTGGCGCACACTACTCAGACTCCGTGAAGGGC

CGGTTCACCATCTCCAGAGACAATTCCAAGAACACGCTGTATCTGCAAAT

GAACAGCCTGAGAGCCGAGGACACGGCCGTGTATTACTGTGCGAGAGATC

GACTGGCACGATGGGTCGACTACGTTATGGACGTCTGGGGCCAGGGCACC

CTGGTCACGGTCTCCTCAGGCTCAGCA-3'

VH (Heavy Chain Variable region) protein sequence
of 2SK-35 ScFv (SEQ ID NO: 16)
NH2EVQLLETGGGLVQPGGSLRLSCAASGFTFSDYYMSWVRQAPGKGLEW

VSGLSGFGRGAHYSDSVKGRFTISRDNSKNTLYLQMNSLRAEDTAVYYCA

RDRLARWVDYVMDVWGQGTLVTVSSGSA-COOH

VL (Light Chain Variable region) nucleotide
sequence of 2SK-35 ScFv (SEQ ID NO: 17)
5'GATATCGTGTTGACGCAGTCTCCAGGCACCCTGTCTTTGTCTCCAGGG

GAAAGAGCCACCCTCTCCTGCAGGGCCAATCAGAGTGTTATCAGCAACTT

GGCCTGGTACCAGCAGAAACCTGGCCAGGCTCCCAGGCTCCTCATCTATG

GTGTGTCCAGTAGGGCCACTGGCATCCCAGACAGGTTCAGTGGCAGTGGG

TCTGGGACAGACTTCACTCTCACCATCAGCNGACNGGAGCCTGAAGATTT

TGCAGTGTATTACTGTCAAAACTATAACAGTGCCCCTCGGANGTTCGGCC

AAGGGACCAAACTGGAAATGAAAGCG-3'

VL (Light Chain Variable region) protein sequence
of 2SK-35 ScFv (SEQ ID NO: 18)
NH2DIVLTQSPGTLSLSPGERATLSCRANQSVISNLAWYQQKPGQAPRLL

IYGVSSRATGIPDRFSGSGSGTDFTLTISXXEPEDFAVYYCQNYNSAPRX

FGQGTKLEIKA-COOH

VH (Heavy Chain Variable region) nucleotide
sequence of 2SK-80 ScFv (SEQ ID NO: 19)
5'GAGGTGCAGCTGTTGGAGTCTGGGGGAGGCTTGGTACAGCCTGGGGGG

TCCCTGAGACTCTCCTGTGCAGCCTCTGGATTCACCTTCCGTAATTATGC

TATTCACTGGATCCGCCAGGCTCCAGGGAAGGGCTGGAGTGGGTTTCACC

ATCTCCAGAGACAATTCCACACGCTGTATCTGCAAATGAACAGCCTGAGA

GCCGAGGACACGGCCGTGTATTACTGTCAAGACGACCGTATAGTGGGAG

GTTCGACCCCTGGGGCCAGGGCACCCTGGTCACAGTCTCCTCAGGCTCA

GCA-3'

VH (Heavy Chain Variable region) protein sequence
of 2SK-80 ScFv (SEQ ID NO: 20)
NH2EVQLLESGGGLVQPGGSLRLSCAASGFTFRNYAIHWIRQAPGKGWSG

FHHLRQRQFHTLYLQMNSLRAEDTAVYYCARRPYSGRFDPWGQGTLVTVSS

GSA-COOH

VL (Light Chain Variable region) nucleotide
sequence of 2SK-80 ScFv (SEQ ID NO: 21)
5'GATATCGTGCTGACTCAGCCACCCTCAGCGTCTGGGACCCCCGGGCAG

AGGGTCACCATCTCCTGTACTGGAAGCCGGTCCAACATCGGAGATAATGC

TGTAAACTGGTAGCAGCAGCTCCCAGGAAAGGCTCCCAAACTCCTCATCT

ATGGTAACAGCAATCGGCCCTCAGGGGTCCCTGACCGGTTCTCTGGCTCC

AAGTCTGGCACCTCAGCCTCCCTGGCCATCAGTGGGCTCCGGTCCGAGGA

TGAGGCTGATTATTACTGTCAGGCGTGGGACAGGACCAATTATGTCTTCG

GAACTGGGACCAAGCTGACCGTCCTCGCG-3'

VL (Light Chain Variable region) protein sequence
of 2SK-80 ScFv (SEQ ID NO: 22)
NH2DIVLTQPPSASGTPGQRVTISCTGSRSNIGDNAVNWYQQLPGKAPKL

LIYGNSNRPSGVPDRFSGSKSGTSASLAISGLRSEDEADYYCQAWDRTNY

VFGTGTKLTVLA-COOH

VH (Heavy Chain Variable region) nucleotide
sequence of 2SK-86 ScFv (SEQ ID NO: 23)
5'GAGGTGCAGCTGTTGGAGTCTGGGGGAGGCTTGGTACAGCCTGGGGGG

TCCCTGAGACTCTCCTGTGCAGCCTCTGGATTCACCTTCAGTAGCGCATG

GATGAGTTGGGTCCGCCAGGCTCCAGGGAAGGGGCTGGAGTGGGTTTCAT

CCATTAGTCGCAGCAGTCGTTACATTTTCTATGCAGACTCAGTGAAGAGC

CGGTTCACCATCTCCAGAGACAATTCCAAGAACACGCTGTATCTGCAAAT

GAACAGCCTGAGAGCCGAGGACACAGCCGTGTATTACTGTGCGAGACATA

GGCGGCCCCTGAATTTTTGGAGTGGTTCTAAATCCCGCATCCCGACCTGG

TTCGACCCCTGGGGCCAGGGCACCCTGGTCACGGTCTCTTCAGGCTCA

GCA-3'

-continued

VH (Heavy Chain Variable region) protein sequence
of 2SK-86 ScFv
(SEQ ID NO: 24)
NH₂EVQLLESGGGLVQPGGSLRLSCAASGFTFSSAWMSWVRQAPGKGLEW

VSSISRSSRYIFYADSVKSRFTISRDNSKNTLYLQMNSLRAEDTAVYYCA

RHRRPLNFWSGSKSRIPTWFDPWGQGTLVTVSSGSA-COOH

VL (Light Chain Variable region) nucleotide
sequence of 2SK-86 ScFv
(SEQ ID NO: 25)
5'GATATCGTGTTGACGCAGTCTCCAGGCACCCTGTGTTTGTCTCCAGGG

GAAAGAGCCACCCTCTCCTGCAGGGCCAGTCAGAGTATTAGTAGCTTCTT

AGCCTGGTACCAGCAGAAAGCTGGCCAGGCTCCCAGGCTCCTCATCTATG

ATCCATCCAACAGGGCCACTGGCATCCCAGACAGGTTCAGTGGCAGTGGG

TCTGGGACAGACTTCACTCTCACCATCAGCAGACTGGAGCCTGAAGATTT

TGCAGTTTATTACTGTCAACAGAGTAACATTTTCCCCCGGAAGTTCGGCC

AAGGGANNNAGCTGGAAANGAAAGCG-3'

VL (Light Chain Variable region)protein sequence
of 2SK-86 ScFv
(SEQ ID NO: 26)
NH₂DIVLTQSPGTLSLSPGERATLSCRASQSISSFLAWYQQKPGQAPRLL

IYDASNRATGIPDRFSGSGSGTDFTLTISRLEPEDFAVYYCQQSNIFPRK

FGQGXXLEXKA-COOH

In spite of the fact that the sequences of the VH and VL regions of ScFv-SK-34 differ from those of ScFv-SK-35, the two mAbs both bind preferentially and with high affinity to a peptide consisting of SEQ ID NO:1 and both mAbs were positive in the syncytia blocking assay. Any single strand mAb selected by a method of the invention is expected to exhibit the desired functional properties, although the sequences of the mAbs may differ.

Figure 18:
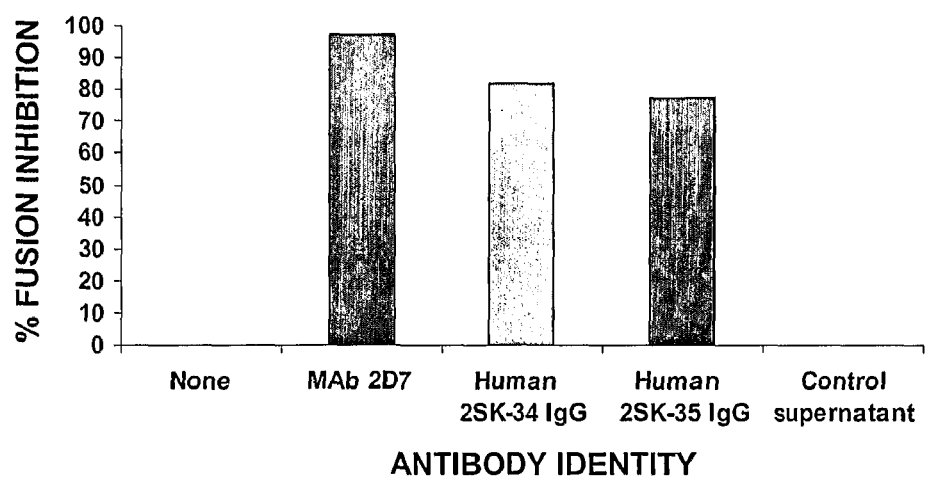
FIG. 18 shows that whole human IgG anti-2SK epitope in CCR5 inhibits HIV syncytia formation by HIV-1 envelopes with human CCR5 expressing cells.

Whole (full-size, bivalent) human monoclonal IgG1 antibodies were "derived from" the single stranded antibodies ScFv-34 and ScFv-35, using a procedure that can be used to derive a whole human monoclonal antibody from any single stranded antibody of interest. ScFv-34 and ScFv-35 were converted to whole (full-size, bivalent) human monoclonal IgG1 antibodies as follows: The VH and VL genes for each antibody were amplified and cloned in separate mammalian expression vectors encoding the respective remaining gene of the heavy chain (constant domains-CH1 and Fc portion of IgG) or light chain (constant domain of light chain, both kappa and lambda), under the control of the CMV promoter (vectors developed by Itai Benhar). Other promoters, both natural and synthetic, in any suitable vector, can also be used for this purpose. Two plasmids (one encoding the heavy chain and the other the light chain) for each antibody were co-transfected into one of the mammalian cell lines, CHO-dhfr-, CHO-K1 or 293. (Any cell line, mammalian or non-mammalian, can be used to produce antibodies, using standard tissue culture and antibody production techniques.) The antibodies in the culture supernatants were purified by standard chromatograph and protein purification techniques, including but not limited to concentration, size exclusion, gel filtration and affinity chromatography. FIG. 18 shows that both of these whole human IgG antibodies inhibit HIV syncytia formation by HIV envelopes with human CCR5 expressing cells.

The invention includes a combination of nucleic acids (a kit; a system) for producing a whole antibody of the invention, comprising a first expression vector that comprises sequences encoding the VH region of the antibody and a second expression vector that comprises sequences encoding the VL region of the antibody. Vectors as described above may be used. The two vectors can then be co-transfected into a host cell and the whole antibody isolated, e.g. as described above. Alternatively, the coding sequences for the VH and VL regions may be on the same expression vector.

Example IV

A Mimotope for the Rhesus CCR5 Sequence, and Polyclonal Antibodies Generated Against the Peptide Based on the alignment of CCR5 sequences from different species shown below, we designed a peptide sequence from the Rhesus CCR5 sequence based on the human CCR5 sequence recognized by MAb 2D7. The alignment of the three CCR5 sequences is shown below:

```
Human CCR5    MDYQVSSP--IYDINYYTSEPCQKINVKQIAARLLPPLYSLVFIFGFVGNMLVILILINC
Rhesus CCR5   MDYQVSSP--TYDIDYYTSEPCQKINVKQIAARLLPPLYSLVFIFGFVGNILVVLILINC
Mouse CCR5    MDFQGSVPTYSYDIDYGMSAPCQKINVKQIAAQLLPPLYSLVFIFGFVGNMMVFLILISC Human CCR5    KRLKSMTDIYLLNLAISDLFFLLTVPFWAHYAAAQWDFGNTMCQLLTGLYFIGFFSGIFF
Rhesus CCR5   KRLKSMTDIYLLNLAISDLLFLLTVPFWAHYAAAQWDFGNTMCQLLTGLYFIGFFSGIFF
Mouse CCR5    KKLKSVTDIYLLNLAISDLLFLLTLPFWAHYAANEWVFGNIMCKVFTGLYHIGYFGGIFF ECL-2
Human CCR5    IILLTIDRYLAVVHAVFALKARTVTFGVVTSVITWVVAVFASLPGIIFTRS QKEGL HYTC
Rhesus CCR5   IILLTIDRYLAIVHAVFALKARTVTFGVVTSVITWVVAVFASLPGIIFTRS QREGL HYTC
Mouse CCR5    IILLTIDRYLAIVHAVFALKVRTVNFGVITSVVTWAVAVFASLPEIIFTRS QKEGF HYTC ECL-2
Human CCR5    SSHFPYSQYQFWKNFQTL KIVILGLVLPLLVMVICYSGILKTLLRCRNEKKRHRAVRLIF
Rhesus CCR5   SSHFPYSQYQFWKNFQTL KMVILGLVLPLLVMVICYSGILKTLLRCRNEKKRHRAVRLIF
Mouse CCR5    SPHFPHTQYHFWKSFQTL KMVILSLILPLLVMVICYSGILHTLFRCRNEKKRHRAVRLIF Human CCR5    TIMIVYFLFWAPYNIVLLLNTFQEFFGLNNCSSSNRLDQAMQVTETLGMTHCCINPIIYA
Rhesus CCR5   TIIIVYFLFWAPYNIVLLLNTFQEFFGLNNCSSSNRLDQAMQVTETLGMTHCCMNPIIYA
Mouse CCR5    AIMIVYFLFWTPYNIVLLLTTFQEFFGLNNCSSSNRLDQAMQATETLGMTHCCLNPVIYA
```

The human sequence is SEQ ID NO:27; the Rhesus sequence is SEQ ID NO:28; and the mouse sequence is SEQ ID NO:29.

The sequence of the rhesus-based peptide (Rh-2D7-2SK) is: E-W-Q-R-E-G-L-V-T-L-W-L (SEQ ID NO:30). This sequence differs from SEQ ID NO:1 at position 4: the Rhesus-based sequence has an R at that position, whereas the human-based sequence has a K at that position.

mAb 2D7 does not bind to Rhesus CCR5 on Rhesus PBMC's and does not inhibit SIV infection of Rhesus PBMC or syncytia formation. By contrast, rabbit antibodies generated against the Human 2SK sequence [Rα2SK] showed moderate inhibition of SIV-mediated fusion of Rhesus PBMC compared to HIV env mediated fusion of human PM1 cells. Moreover, rabbit antibodies generated on immunization of the Rhesus-derived corresponding 2SK peptide sequence [Rα2SK(Rh)] showed a higher specificity of inhibition of SIV mediated fusion of Rhesus PBMC, equivalent to what was observed for inhibition of human PM1 with HIV with the rabbit anti-human 2SK peptide sequence. These data are presented in Table 2.

TABLE 2

A rabbit anti-2D7 mimotope for the Rhesus CCR5 sequence (Rα2SK(Rh)) inhibits SIV239 Env-mediated fusion with rhesus PBMC better than a rabbit anti-2SK mimotope based on the human CCR5 sequence (stimulated with PHA/IL2 for 3 days).

| Target cells | Effector cells (HIV/SIV Env) | Inhibitor (µg/ml) | No. of Syncytia | % Inhibition |
|---|---|---|---|---|
| PM1 | 12E1/BaL | None | 475 ± 68 | |
| | | 2D7 (20) | 5 ± 2 | 99% |
| | | NRS (25) | 487 ± 73 | 0% |
| | | Rα2SK(25) | 191 ± 22 | 60% |
| | | Rα2SK(Rh)(25) | 247 ± 5 | 48% |
| Rhesus PBMC (#810) | 12E1/SIV$_{239}$ | None | 270 ± 42 | |
| | | 2D7 (20) | 258 ± 5 | 4% |
| | | NRS (25) | 285 ± 30 | 0% |
| | | Rα2SK(25) | 156 ± 39 | 42% |
| | | Rα2SK(Rh)(25) | 107 ± 15 | 60% |

"NRS" refers to normal rabbit sera (prebleed rabbit IgG).

This study indicates that this rhesus-based peptide can be used as an immunogen to generate relevant monoclonal/polyclonal antibodies in various species including monkeys, rabbit, mouse, rat, humans, in vitro with cell lines and by other methods. Furthermore, the peptide can be used for vaccine development; or it can serve as the basis for designing drugs, vaccines, chemicals, biomolecules, etc, based on its sequence and/or structure. The peptide, or variants thereof (as discussed herein with regard to peptides comprising or consisting of SEQ ID NO:1), can be used in any of the methods or applications discussed herein with regard to the human-based peptide. Similarly, antibodies, including polyclonal, monoclonal ScFv, and whole monoclonal IgG antibodies against the Rhesus-based peptide can be generated and used as described herein with regard to antibodies against the human-based peptide.

A reagent (such as an antibody against this rhesus-derived peptide) which reacts with monkey CCR5 is particularly valuable for proof-of-concept studies on putative anti-HIV therapies in monkeys.

Example V

Purification of ScFv Antibodies of the Invention

Soluble antibodies, such as ScFv-34 and the whole antibodies corresponding to ScFv-34 and ScFv-35 are purified by conventional procedures, such as affinity chromatography. Insoluble antibodies, such as ScFv-35 are purified by a procedure that involves large scale denaturation of ScFv inclusion bodies; gradient dialysis of the refolded protein; protein concentration of the dialyzed material; H is metal affinity chromatography; gel filtration chromatography; polymixin-B-chromatography (for LPS); gel filtration chromatography; and ELISA followed by a second affinity column and gel filtration chromatography. The purified antibodies are then used in vitro and in vivo studies. For example, testing is carried out for inhibition of HIV primary isolates.

Example VI

Testing Antibodies of the Invention In Vivo

Human neutralizing antibodies as described in the previous Examples are produced and purified on a large scale. They are then tested in in vivo models of HIV infection, including SCID-Hu mouse and Rhesus monkeys, using conventional procedures.

It is expected that the antibodies will exhibit sufficient antiviral activity to be used in passive immunoprophylaxis; as mucosal microbicides; and/or in immunotherapy of HIV-, SHIV- or SIV-infected individuals.

Example VII

Testing Peptides of the Invention for Vaccine Activity

Peptides of the invention (e.g. a peptide comprising or consisting of SEQ ID NO:1 or SEQ ID NO:30, or an active variant of one of those sequences) are conjugated to suitable adjuvants, such as LSK, alum, CpGs, or are generated as fusion proteins that comprise immunogenic sequences. The conjugated peptides are then administered to animal models, and are evaluated for their ability to protect the animals against SHIV infection. These methods are conventional. See, e.g., Bogers et al. (2004) *AIDS* 18, 25-36 or Chakerian et al. (2004) *J. Virol* 78, 4037-47. It is expected that the peptides will elicit substantial protection. See Bogers et al. (2004) and Chakerian et al. (2004) supra for examples in which CCR5-related peptides act as protective vaccines in monkey models.

Compositions and methods described in US patent publications 2001 0034432 and 2003 0180284 and U.S. Pat. No. 6,692,938 can also be applied to the present invention.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, including U.S. provisional application 60/560,703, cited above and in the figures are hereby incorporated by reference.

We claimed:

1. An isolated peptide consisting of the contiguous sequence E-W-Q-K-E-G-L-V-T-L-W-L (SEQ ID NO:1) or the contiguous sequence E-W-O-R-E-G-L-V-T-L-W-L (SEQ ID NO:30), wherein the peptide closely mimics a conformational epitope of CCR5 that is involved in human immunodeficiency virus (HIV), simian-human immunodeficiency virus (SHIV) or simian immunodeficiency virus (SIV) infection.

2. A pharmaceutical composition comprising a peptide of claim 1 and a pharmaceutically acceptable carrier.

3. A kit comprising a peptide of claim 1, in a container.

4. A method for screening for an agent that inhibits CCR5-mediated infectivity of human immunodeficiency virus (HIV), simian-human immunodeficiency virus (SHIV) or simian immunodeficiency virus (SIV), comprising contacting candidate agents with a peptide of claim 1, under conditions that allow for binding of the candidate agents to the peptide of claim 1, measuring the degree of binding of the candidate agents to the peptide of claim 1, and identifying agents that binds preferentially and with a high affinity to the peptide of claim 1, wherein a candidate agent that binds to the peptide of claim 1 preferentially and with high affinity is a putative agent that inhibits CCR5-mediated infectivity of HIV, SHIV or SIV.

5. The method of claim 4, wherein the agent is a mAb, and the agent is identified by screening a library of candidate mAbs.

6. The method of claim 4, wherein the agent is a human mAb, and the agent is identified by screening a library of candidate human mAbs.

7. The method of claim 4, wherein the agent is a small molecule antagonist or ligand of CCR5.

* * * * *

SEQUENCE LISTING

<160> NUMBER OF SEQ ID NOS: 30

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Trp Gln Lys Glu Gly Leu Val Thr Leu Trp Leu
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Lys Glu Gly Leu
1               5

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Gly Arg Ala Ala Arg Ile Gly Phe Pro Gly Ala Tyr Thr Thr Lys
1               5                   10                  15

Asn Gly

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Trp Gln Lys Glu Gly Leu Val Thr Leu Trp Leu Gly Gly Gly Gly
1               5                   10                  15

Ser Cys

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Trp Gln Lys Glu Gly Leu Val Ala Leu Trp Leu Gly Gly Gly Gly
1               5                   10                  15

Ser Cys

```
<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Trp Gln Lys Glu Gly Leu Val Thr Ala Trp Leu Gly Gly Gly Gly
1               5                   10                  15

Ser Cys

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Trp Gln Lys Glu Gly Leu Val Ala Ala Trp Leu Gly Gly Gly Gly
1               5                   10                  15

Ser Cys

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Trp Gln Arg Glu Gly Leu Val Thr Leu Trp Leu Gly Gly Gly Gly
1               5                   10                  15

Ser Cys

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Leu Trp Leu Gly Trp Thr Glu Leu Glu Gly Val Lys Gly Gly Gly
1               5                   10                  15

Ser Cys

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Cys Ala Leu Asp Gly Asp Phe Gly Trp Leu Ala Pro Ala Cys
1               5                   10                  15
```

<210> SEQ ID NO 11
<211> LENGTH: 366
<212> TYPE: DNA
<213> ORGANISM: Homo sapiens

<400> SEQUENCE: 11

```
gaggtgcagc tgttggagtc tgggggaggc ttggtacagc ctgggggtc cctgagactc      60 tcctgtgcag cctctggatt cacctttgat gattatggaa tgagctgggt ccgccaggct     120
ccagggaagg ggctggagtg ggtctcagtt attagtgcta gtggtggtag cacatactac    180
gcagactccg tgaatggccg gttcaccatc tccagagaca attccaagaa cacgctgtat    240
ctgcaaatga acagcctgag agccgaggac acggccgtgt attactgtgc aagatacttg    300
cctggtcttt gggctatgga cgtctggggc cagggcaccc tggtcacagt ctcttcaggc    360
tcagca                                                                366
```

<210> SEQ ID NO 12
<211> LENGTH: 122
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Val Ile Ser Ala Ser Gly Gly Ser Thr Tyr Tyr Ala Asp Ser Val
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Leu Pro Gly Leu Trp Ala Met Asp Val Trp Gly Gln Gly
            100                 105                 110

Thr Leu Val Thr Val Ser Ser Gly Ser Ala
        115                 120

<210> SEQ ID NO 13
<211> LENGTH: 333
<212> TYPE: DNA
<213> ORGANISM: Homo sapiens

<400> SEQUENCE: 13

```
gatatcgtgc tgactcagcc accctcagcg tctgggaccc ccgggcagag ggtcaccatc      60
tcttgtaccg gaagcagatc caacattggg aagaattatg tttcctggta ccagcagctt    120
ccaggaaagg ctcccaaact cctcatctat aagaattatc agcggccctc aggggtccct    180
gaccggttct ctggctccaa gtctggcacc tcagcctccc tggccatcag tgggctgcgg    240
tccgaggatg aggctgatta ttactgtgca gcatgggatg acagtctgag tggttgggtg    300
ttcggcggaa gcacccagct caccgtcctc gcg                                  333
```

<210> SEQ ID NO 14
<211> LENGTH: 111
<212> TYPE: PRT
<213> ORGANISM: Homo sapiens

<400> SEQUENCE: 14

Asp Ile Val Leu Thr Gln Pro Pro Ser Ala Ser Gly Thr Pro Gly Gln
1               5                   10                  15

Arg Val Thr Ile Ser Cys Thr Gly Ser Arg Ser Asn Ile Gly Lys Asn
            20                  25                  30

Tyr Val Ser Trp Tyr Gln Gln Leu Pro Gly Lys Ala Pro Lys Leu Leu
        35                  40                  45

Ile Tyr Lys Asn Tyr Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Ser Thr Gln Leu Thr Val Leu Ala
            100                 105                 110

<210> SEQ ID NO 15
<211> LENGTH: 375
<212> TYPE: DNA
<213> ORGANISM: Homo sapiens

<400> SEQUENCE: 15
gaggtgcagc tgttggagac tgggggaggc ttggtacagc ctgggggggtc cctgagactc      60
tcctgtgcag cctctggatt caccttcagt gactattaca tgagctgggt ccgccaggct     120
ccagggaagg gctggagtg gtttcagga ctgagtggtt ttggtcgtgg cgcacactac      180
tcagactccg tgaagggccg gttcaccatc tccagagaca attccaagaa cacgctgtat     240
ctgcaaatga acagcctgag agccgaggac acggccgtgt attactgtgc gagagatcga     300
ctggcacgat gggtcgacta cgttatggac gtctggggcc agggcaccct ggtcacggtc     360
tcctcaggct cagca                                                      375

<210> SEQ ID NO 16
<211> LENGTH: 125
<212> TYPE: PRT
<213> ORGANISM: Homo sapiens

<400> SEQUENCE: 16

Glu Val Gln Leu Leu Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Leu Ser Gly Phe Gly Arg Gly Ala His Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Ala Arg Trp Val Asp Tyr Val Met Asp Val Trp
            100                 105                 110

Gly Gln Gly Thr Leu Val Thr Val Ser Ser Gly Ser Ala
        115                 120                 125

```
<210> SEQ ID NO 17
<211> LENGTH: 324
<212> TYPE: DNA
<213> ORGANISM: Homo sapiens
<220> FEATURE:
<221> NAME/KEY: modified_base
<222> LOCATION: (229)
<223> OTHER INFORMATION: a, c, t, g, unknown or other
<220> FEATURE:
<221> NAME/KEY: modified_base
<222> LOCATION: (233)
<223> OTHER INFORMATION: a, c, t, g, unknown or other
<220> FEATURE:
<221> NAME/KEY: modified_base
<222> LOCATION: (290)
<223> OTHER INFORMATION: a, c, t, g, unknown or other

<400> SEQUENCE: 17
gatatcgtgt tgacgcagtc tccaggcacc ctgtctttgt ctccagggga aagagccacc      60
ctctcctgca gggccaatca gagtgttatc agcaacttgg cctggtacca gcagaaacct     120
ggccaggctc ccaggctcct catctatggt gtgtccagta gggccactgg catcccagac     180
aggttcagtg gcagtgggtc tgggacagac ttcactctca ccatcagcng acnggagcct     240
gaagattttg cagtgtatta ctgtcaaaac tataacagtg cccctcggan gttcggccaa     300
gggaccaaac tggaaatcaa agcg                                            324

<210> SEQ ID NO 18
<211> LENGTH: 108
<212> TYPE: PRT
<213> ORGANISM: Homo sapiens
<220> FEATURE:
<221> NAME/KEY: MOD_RES
<222> LOCATION: (77)..(78)
<223> OTHER INFORMATION: Variable amino acid
<220> FEATURE:
<221> NAME/KEY: MOD_RES
<222> LOCATION: (97)
<223> OTHER INFORMATION: Variable amino acid

<400> SEQUENCE: 18

Asp Ile Val Leu Thr Gln Ser Pro Gly Thr Leu Ser Leu Ser Pro Gly
1               5                   10                  15

Glu Arg Ala Thr Leu Ser Cys Arg Ala Asn Gln Ser Val Ile Ser Asn
                20                  25                  30

Leu Ala Trp Tyr Gln Gln Lys Pro Gly Gln Ala Pro Arg Leu Leu Ile
            35                  40                  45

Tyr Gly Val Ser Ser Arg Ala Thr Gly Ile Pro Asp Arg Phe Ser Gly
        50                  55                  60

Ser Gly Ser Gly Thr Asp Phe Thr Leu Thr Ile Ser Xaa Xaa Glu Pro
65                  70                  75                  80

Glu Asp Phe Ala Val Tyr Tyr Cys Gln Asn Tyr Asn Ser Ala Pro Arg
                85                  90                  95

Xaa Phe Gly Gln Gly Thr Lys Leu Glu Ile Lys Ala
            100                 105

<210> SEQ ID NO 19
<211> LENGTH: 300
<212> TYPE: DNA
<213> ORGANISM: Homo sapiens

<400> SEQUENCE: 19
gaggtgcagc tgttggagtc tgggggaggc ttggtacagc ctggggggtc cctgagactc      60
tcctgtgcag cctctggatt caccttccgt aattatgcta ttcactggat ccgccaggct     120
```

-continued

```
ccagggaagg gctggagtgg gtttcaccat ctccagagac aattccacac gctgtatctg    180
caaatgaaca gcctgagagc cgaggacacg gccgtgtatt actgtgcaag acgaccgtat    240
agtgggaggt cgacccctg gggccagggc accctggtca cagtctcctc aggctcagca    300
```

<210> SEQ ID NO 20
<211> LENGTH: 100
<212> TYPE: PRT
<213> ORGANISM: Homo sapiens

<400> SEQUENCE: 20

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Ile His Trp Ile Arg Gln Ala Pro Gly Lys Gly Trp Ser Gly Phe
        35                  40                  45

His His Leu Gln Arg Gln Phe His Thr Leu Tyr Leu Gln Met Asn Ser
    50                  55                  60

Leu Arg Ala Glu Asp Thr Ala Val Tyr Tyr Cys Ala Arg Arg Pro Tyr
65                  70                  75                  80

Ser Gly Arg Phe Asp Pro Trp Gly Gln Gly Thr Leu Val Thr Val Ser
                85                  90                  95

Ser Gly Ser Ala
100
```

<210> SEQ ID NO 21
<211> LENGTH: 327
<212> TYPE: DNA
<213> ORGANISM: Homo sapiens

<400> SEQUENCE: 21

```
gatatcgtgc tgactcagcc accctcagcg tctgggaccc ccgggcagag ggtcaccatc     60
tcctgtactg gaagccggtc caacatcgga gataatgctg taaactggta ccagcagctc    120
ccaggaaagg ctcccaaact cctcatctat ggtaacagca tcggccctc aggggtccct    180 gaccggttct ctggctccaa gtctggcacc tcagcctccc tggccatcag tgggctccgg    240
tccgaggatg aggctgatta ttactgtcag gcgtgggaca ggaccaatta tgtcttcgga    300
actgggacca agctgaccgt cctcgcg                                       327
```

<210> SEQ ID NO 22
<211> LENGTH: 109
<212> TYPE: PRT
<213> ORGANISM: Homo sapiens

<400> SEQUENCE: 22

```
Asp Ile Val Leu Thr Gln Pro Pro Ser Ala Ser Gly Thr Pro Gly Gln
1               5                   10                  15

Arg Val Thr Ile Ser Cys Thr Gly Ser Arg Ser Asn Ile Gly Asp Asn
            20                  25                  30

Ala Val Asn Trp Tyr Gln Gln Leu Pro Gly Lys Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80
```

```
Ser Glu Asp Glu Ala Asp Tyr Tyr Cys Gln Ala Trp Asp Arg Thr Asn
                85                  90                  95

Tyr Val Phe Gly Thr Gly Thr Lys Leu Thr Val Leu Ala
            100                 105

<210> SEQ ID NO 23
<211> LENGTH: 399
<212> TYPE: DNA
<213> ORGANISM: Homo sapiens

<400> SEQUENCE: 23
gaggtgcagc tgttggagtc tgggggaggc ttggtacagc ctgggggggtc cctgagactc      60 tcctgtgcag cctctggatt caccttcagt agcgcatgga tgagttgggt ccgccaggct     120
ccagggaagg ggctggagtg ggtttcatcc attagtcgca gcagtcgtta cattttctat     180
gcagactcag tgaagagccg gttcaccatc tccagagaca attccaagaa cacgctgtat     240
ctgcaaatga acagcctgag agccgaggac acagccgtgt attactgtgc gagacatagg     300 cggccccctga attttggag tggttctaaa tcccgcatcc cgacctggtt cgacccctgg     360
ggccagggca ccctggtcac ggtctcttca ggctcagca                            399

<210> SEQ ID NO 24
<211> LENGTH: 133
<212> TYPE: PRT
<213> ORGANISM: Homo sapiens

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Trp Met Ser Trp Val Arg Gln Ala Pro Gly Lys Gly Leu Glu Trp Val
        35                  40                  45

Ser Ser Ile Ser Arg Ser Ser Arg Tyr Ile Phe Tyr Ala Asp Ser Val
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Arg Pro Leu Asn Phe Trp Ser Gly Ser Lys Ser Arg
            100                 105                 110

Ile Pro Thr Trp Phe Asp Pro Trp Gly Gln Gly Thr Leu Val Thr Val
        115                 120                 125

Ser Ser Gly Ser Ala
    130

<210> SEQ ID NO 25
<211> LENGTH: 324
<212> TYPE: DNA
<213> ORGANISM: Homo sapiens
<220> FEATURE:
<221> NAME/KEY: modified_base
<222> LOCATION: (305)..(307)
<223> OTHER INFORMATION: a, c, t, g, unknown or other
<220> FEATURE:
<221> NAME/KEY: modified_base
<222> LOCATION: (317)
<223> OTHER INFORMATION: a, c, t, g, unknown or other

<400> SEQUENCE: 25
```

-continued

```
gatatcgtgt tgacgcagtc tccaggcacc ctgtctttgt ctccagggga aagagccacc      60
ctctcctgca gggccagtca gagtattagt agcttcttag cctggtacca gcagaaacct     120
ggccaggctc ccaggctcct catctatgat gcatccaaca gggccactgg catcccagac     180
aggttcagtg gcagtgggtc tgggacagac ttcactctca ccatcagcag actggagcct     240
gaagattttg cagtttatta ctgtcaacag agtaacattt tccccggaa gttcggccaa      300 gggannnagc tggaaangaa agcg                                            324
```

<210> SEQ ID NO 26
<211> LENGTH: 108
<212> TYPE: PRT
<213> ORGANISM: Homo sapiens
<220> FEATURE:
<221> NAME/KEY: MOD_RES
<222> LOCATION: (102)..(103)
<223> OTHER INFORMATION: Variable amino acid
<220> FEATURE:
<221> NAME/KEY: MOD_RES
<222> LOCATION: (106)
<223> OTHER INFORMATION: Variable amino acid

<400> SEQUENCE: 26

```
Asp Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Asn Ile Phe Pro Arg
                85                  90                  95

Lys Phe Gly Gln Gly Xaa Xaa Leu Glu Xaa Lys Ala
            100                 105
```

<210> SEQ ID NO 27
<211> LENGTH: 298
<212> TYPE: PRT
<213> ORGANISM: Homo sapiens

<400> SEQUENCE: 27

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
```

```
            115                 120                 125
Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala
    290                 295

<210> SEQ ID NO 28
<211> LENGTH: 298
<212> TYPE: PRT
<213> ORGANISM: Macaca mulatta

<400> SEQUENCE: 28

Met Asp Tyr Gln Val Ser Ser Pro Thr Tyr Asp Ile Asp Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Ile Leu Val Val Leu Ile Leu Ile Asn Cys Lys Arg Leu Lys Ser Met
    50                  55                  60

Thr Asp Ile Tyr Leu Leu Asn Leu Ala Ile Ser Asp Leu Leu Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Ile Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Arg Glu Gly Leu His Tyr
                165                 170                 175

Thr Cys Ser Ser His Phe Pro Tyr Ser Gln Tyr Gln Phe Trp Lys Asn
            180                 185                 190
```

```
Phe Gln Thr Leu Lys Met Val Ile Leu Gly Leu Val Leu Pro Leu Leu
            195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Ile Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Met Asn Pro Ile Ile Tyr Ala
    290                 295
```

<210> SEQ ID NO 29
<211> LENGTH: 300
<212> TYPE: PRT
<213> ORGANISM: Mus musculus

<400> SEQUENCE: 29

```
Met Asp Phe Gln Gly Ser Val Pro Thr Tyr Ser Tyr Asp Ile Asp Tyr
1               5                   10                  15

Gly Met Ser Ala Pro Cys Gln Lys Ile Asn Val Lys Gln Ile Ala Ala
            20                  25                  30

Gln Leu Leu Pro Pro Leu Tyr Ser Leu Val Phe Ile Phe Gly Phe Val
        35                  40                  45

Gly Asn Met Met Val Phe Leu Ile Leu Ile Ser Cys Lys Lys Leu Lys
    50                  55                  60

Ser Val Thr Asp Ile Tyr Leu Leu Asn Leu Ala Ile Ser Asp Leu Leu
65                  70                  75                  80

Phe Leu Leu Thr Leu Pro Phe Trp Ala His Tyr Ala Ala Asn Glu Trp
                85                  90                  95

Val Phe Gly Asn Ile Met Cys Lys Val Phe Thr Gly Leu Tyr His Ile
            100                 105                 110

Gly Tyr Phe Gly Gly Ile Phe Phe Ile Ile Leu Leu Thr Ile Asp Arg
        115                 120                 125

Tyr Leu Ala Ile Val His Ala Val Phe Ala Leu Lys Val Arg Thr Val
    130                 135                 140

Asn Phe Gly Val Ile Thr Ser Val Val Thr Trp Ala Val Ala Val Phe
145                 150                 155                 160

Ala Ser Leu Pro Glu Ile Ile Phe Thr Arg Ser Gln Lys Glu Gly Phe
                165                 170                 175

His Tyr Thr Cys Ser Pro His Phe Pro His Thr Gln Tyr His Phe Trp
            180                 185                 190

Lys Ser Phe Gln Thr Leu Lys Met Val Ile Leu Ser Leu Ile Leu Pro
        195                 200                 205

Leu Leu Val Met Val Ile Cys Tyr Ser Gly Ile Leu His Thr Leu Phe
    210                 215                 220

Arg Cys Arg Asn Glu Lys Lys Arg His Arg Ala Val Arg Leu Ile Phe
225                 230                 235                 240

Ala Ile Met Ile Val Tyr Phe Leu Phe Trp Thr Pro Tyr Asn Ile Val
                245                 250                 255

Leu Leu Leu Thr Thr Phe Gln Glu Phe Phe Gly Leu Asn Asn Cys Ser
            260                 265                 270
```

-continued

```
Ser Ser Asn Arg Leu Asp Gln Ala Met Gln Ala Thr Glu Thr Leu Gly
        275                 280                 285

Met Thr His Cys Cys Leu Asn Pro Val Ile Tyr Ala
    290                 295                 300

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Trp Gln Arg Glu Gly Leu Val Thr Leu Trp Leu
1               5                   10
```